United States Patent
Staffler et al.

(10) Patent No.: US 10,344,062 B2
(45) Date of Patent: Jul. 9, 2019

(54) METHOD OF INHIBITING C5A

(71) Applicant: AFFIRIS AG, Vienna (AT)

(72) Inventors: Guenther Staffler, Vienna (AT); Christine Landlinger, Vienna (AT); Frank Mattner, Vienna (AT)

(73) Assignee: AFFIRIS AG, Vienna (AT)

( * ) Notice: Subject to any disclaimer, the term of this patent is extended or adjusted under 35 U.S.C. 154(b) by 291 days.

(21) Appl. No.: 14/402,145

(22) PCT Filed: May 23, 2013

(86) PCT No.: PCT/EP2013/060618
§ 371 (c)(1),
(2) Date: Nov. 19, 2014

(87) PCT Pub. No.: WO2013/174920
PCT Pub. Date: Nov. 28, 2013

(65) Prior Publication Data
US 2015/0166620 A1    Jun. 18, 2015

(30) Foreign Application Priority Data
May 23, 2012    (EP) .................................... 12169088

(51) Int. Cl.
A61K 47/64    (2017.01)
C07K 14/47    (2006.01)
C07K 16/18    (2006.01)
A61K 39/00    (2006.01)

(52) U.S. Cl.
CPC ........ *C07K 14/472* (2013.01); *A61K 39/0005* (2013.01); *A61K 47/643* (2017.08); *A61K 47/646* (2017.08); *A61K 47/6415* (2017.08); *C07K 16/18* (2013.01); *A61K 2039/58* (2013.01); *C07K 2317/34* (2013.01); *C07K 2317/76* (2013.01)

(58) Field of Classification Search
CPC .............. A61K 38/1725; C07K 14/472; C12Y 304/21043; G01N 2333/4716; Y10S 436/821
See application file for complete search history.

(56) References Cited

U.S. PATENT DOCUMENTS 7,538,211 B2 *   5/2009   Benedict .............. C12N 15/115
                                                    436/524
2010/0111995 A1   5/2010   Bachman et al.
2012/0231008 A1   9/2012   Guo et al.

FOREIGN PATENT DOCUMENTS

EP   0245993        11/1987
EP   2 327 725 A1   6/2011
JP   2008-543810    12/2008
WO   WO 90/09162 A2  8/1990
WO   WO 2006/134125 A1  12/2006

OTHER PUBLICATIONS

Anderson et al., J Peptide Res, 49(6):476-483, 1997.*
Monk et al., British Journal of Pharmacology (2007) 152, 429-448.*
Kola et al. Immunotechnology, 2:115-126, 1996.*
Lefeber et al., Chemistry, 7(20):4411-21, Oct. 2001.*
Stevens et al., J Clin Invest; 77(6):1812-1816, Jun. 1986.*
Anderson et al., J Peptide Research, 49:476-481, 1997.*
International Search Report and Written Opinion dated Jul. 1, 2013, in PCT/EP13/060618 filed May 23, 2013.
European Search Report dated Sep. 4, 2012, in European Patent Application No. 12169088.7 filed May 23, 2012.
Nandakumar, et al., "A Recombinant Vaccine Effectively Induces C5a-Specific Neutralizing Antibodies and Prevents Arthritis", Plos One, Public Library of Science, vol. 5, No. 10, XP002637243, Oct. 20, 2010, 11 pages.
Allegretti, et al., "Targeting C5a: Recent Advances in Drug Discovery", Current Medicinal Chemistry, vol. 12, No. 2, 2005, pp. 217-236.
Chen, et al., "The complement system in systemic autoimmune disease", Journal of Autoimmunity, 34, Elsevier, 2010, pp. J276-J286.
Millan, et al., "CpG DNA can induce strong Th1 humoral and cell-mediated immune responses against hepatitis B surface antigen in young mice", Proc. Natl. Acad. Sci. USA, vol. 95, Immunology, Dec. 1998, pp. 15553-15558.
Davis, et al., "CpG DNA Is Potent Enhancer of Specific Immunity in Mice Immunized with Recombinant Hepatitis B Surface Antigen", The Journal of Immunology, 160, 1998, 8 pages.
Fonseca, et al., "Treatment with a C5aR Antagonist Decreases Pathology and Enhances Behavioral Performance in Murine Models of Alzheimer's Disease", The Journal of Immunology, 183, 2009, 10 pages.

(Continued)

*Primary Examiner* — Kimberly Ballard
*Assistant Examiner* — Stacey N MacFarlane
(74) *Attorney, Agent, or Firm* — Oblon, McClelland, Maier & Neustadt, L.L.P.

(57) ABSTRACT

The present invention relates to a vaccine comprising at least one peptide consisting of 7 to 19 amino acid residues consisting of the amino acid sequence $(X_3)_m KDX_2 QLGX_1$ (SEQ ID No. 99), wherein $X_1$ is an amino acid residue selected from the group consisting of alanine, asparagine, glutamine, glycine, histidine, isoleucine, leucine, lysine, methionine, serine, threonine, tyrosine and valine, $X_2$ is an amino acid residue selected from the group consisting of alanine, arginine, histidine, isoleucine, leucine, lysine, methionine, threonine, tyrosine and valine. $X_3$ is (X4)nANISX5 (SEQ ID No. 100) or an N-terminal truncated fragment thereof consisting of 1 to 4 amino acid residues, $X_4$ is VVASQLR (SEQ ID No. 101) or an N-terminal truncated fragment thereof consisting of 1 to 6 amino acid residues, $X_5$ is an amino acid residue selected from the group consisting of alanine, asparagine, glutamine, glutamic acid, histidine, arginine, isoleucine, lysine, methionine, serine and threonine, m is 0 or 1, and n is 0 or 1, wherein said at least one peptide is coupled or fused to a carrier comprising at least one T-cell epitope.

21 Claims, 6 Drawing Sheets
Specification includes a Sequence Listing.

(56) References Cited

OTHER PUBLICATIONS

Jacob, et al., "Inhibition of C5a receptor alleviates experimental CNS lupus", NIH Public Access, J Neuroimmunol. Author Manuscript, 2010, 19 pages.

Klos, et al., "The role of the anaphylatoxins in health and disease", Elsevier, Molecular Immunology, 2009, 14 pages.

Koehl., et al., "A regulatory role for the C5a anaphylatoxin in type 2 immunity in asthma", the Journal of Clinical Investigation, vol. 116, No. 3, Mar. 2006, 14 pages.

Garcia, et al., "Nucleotide sequence and expression of the pneumococcal autolysin gene from its own promoter in *Escherichia coli*", Elsevier, Gene, 43, 1986, pp. 265-272.

McCluskie, et al., "Cutting Edge: CpG DNA Is a Potent Enhancer of Systemic and Mucosal Immune responses Against Hepatitis B Surface Antigen with Intranasal Administration to Mice", The Journal of Immunology, 161,1998, 5 pages.

McGeer, et al., "Inflammation and neurodegeneration in Parkinson's disease", Parkinsonism and Related Disorders, Elsevier, vol. 10, 2004, pp. S3-S7.

Nozaki, et al., "Drusen complement components C3a and C5a promote choroidal neovascularization", PNAS, vol. 103, No. 7, Feb. 14, 2006, pp. 2328-2333.

O'Hagan, et al., "Recent Advances in the Discovery and Delivery of Vaccine Adjuvants", Nature Reviews, Drug Discovery, vol. 2, Sep. 2003, pp. 727-735.

Okroj, et al., "Rheumatoid arthritis and the complement system", Annals of Medicine, vol. 39, 2007, pp. 517-530.

Sato, et al., "Immunostimulatory DNA Sequences Necessary for Effective Intradermal Gene Immunization", Science, vol. 273, Jul. 19, 1996, pp. 352-354.

Singh, et al., "Advances in vaccine adjuvants", Nature Biotechnology, vol. 17, Nov. 1999, pp. 1075-1081.

Singhrao, et al., "Increased Complement Biosynthesis by Microglia and Complement Activation on Neurons in Huntigton's Disease", Experimental Neurology, vol. 159, 1999, pp. 362-376.

Medical Dictionary of molecular cell biology, 1997, p. 11.

The dictionary of molecular cell biology, 1997, p. 11.

Examination Report as received in the corresponding Japanese Patent Application No. 2015-513180 w/English Translation dated Mar. 28, 2017.

* cited by examiner

SEQUENCE LISTING

<160> NUMBER OF SEQ ID NOS: 130

<210> SEQ ID NO 1
<211> LENGTH: 10
<212> TYPE: PRT
<213> ORGANISM: Artificial Sequence
<220> FEATURE:
<223> OTHER INFORMATION: Variotope

<400> SEQUENCE: 1

Ile Ser His Lys Asp Met Gln Leu Gly Arg
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Variotope

<400> SEQUENCE: 2

Ala Asn Ile Ser His Lys Asp Met Gln Leu Gly Arg
1               5                   10

<210> SEQ ID NO 3
<211> LENGTH: 7
<212> TYPE: PRT
<213> ORGANISM: Artificial Sequence
<220> FEATURE:
<223> OTHER INFORMATION: Variotope

<400> SEQUENCE: 3

Lys Asp Met Gln Leu Gly Arg
1               5

<210> SEQ ID NO 4
<211> LENGTH: 19
<212> TYPE: PRT
<213> ORGANISM: Artificial Sequence
<220> FEATURE:
<223> OTHER INFORMATION: Variotope

<400> SEQUENCE: 4

Val Val Ala Ser Gln Leu Arg Ala Asn Ile Ser His Lys Asp Met Gln
1               5                   10                  15

Leu Gly Arg

<210> SEQ ID NO 5
<211> LENGTH: 10
<212> TYPE: PRT
<213> ORGANISM: Artificial Sequence
<220> FEATURE:
<223> OTHER INFORMATION: Variotope

<400> SEQUENCE: 5

Ala Ser His Lys Asp Met Gln Leu Gly Arg
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Variotope

```
<400> SEQUENCE: 6

Ile Ala His Lys Asp Met Gln Leu Gly Arg
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Variotope

<400> SEQUENCE: 7

Ile Ser Ala Lys Asp Met Gln Leu Gly Arg
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Variotope

<400> SEQUENCE: 8

Ile Ser His Ala Asp Met Gln Leu Gly Arg
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Variotope

<400> SEQUENCE: 9

Ile Ser His Lys Ala Met Gln Leu Gly Arg
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Variotope

<400> SEQUENCE: 10

Ile Ser His Lys Asp Ala Gln Leu Gly Arg
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Variotope

<400> SEQUENCE: 11

Ile Ser His Lys Asp Met Ala Leu Gly Arg
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Variotope
```

```
<400> SEQUENCE: 12

Ile Ser His Lys Asp Met Gln Ala Gly Arg
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Variotope

<400> SEQUENCE: 13

Ile Ser His Lys Asp Met Gln Leu Ala Arg
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Variotope

<400> SEQUENCE: 14

Ile Ser His Lys Asp Met Gln Leu Gly Ala
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Variotope

<400> SEQUENCE: 15

Ala Ala Ile Ser His Lys Asp Met Gln Leu Gly Arg
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Variotope

<400> SEQUENCE: 16

Ala Asn Ala Ser His Lys Asp Met Gln Leu Gly Arg
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Variotope

<400> SEQUENCE: 17

Ala Asn Ile Ser Ala Lys Asp Met Gln Leu Gly Arg
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Variotope
```

```
<400> SEQUENCE: 18

Ala Asn Ile Ser His Lys Asp Ala Gln Leu Gly Arg
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Variotope

<400> SEQUENCE: 19

Ala Asn Ile Ser His Lys Asp Met Gln Ala Gly Arg
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Variotope

<400> SEQUENCE: 20

Ala Asn Ile Ser His Lys Asp Met Gln Leu Ala Arg
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Variotope

<400> SEQUENCE: 21

Ala Asn Ile Ser His Lys Asp Met Gln Leu Gly Ala
1               5                   10

<210> SEQ ID NO 22
<211> LENGTH: 7
<212> TYPE: PRT
<213> ORGANISM: Artificial Sequence
<220> FEATURE:
<223> OTHER INFORMATION: Variotope

<400> SEQUENCE: 22

Lys Asp Met Gln Leu Gly Ala
1               5

<210> SEQ ID NO 23
<211> LENGTH: 19
<212> TYPE: PRT
<213> ORGANISM: Artificial Sequence
<220> FEATURE:
<223> OTHER INFORMATION: Variotope

<400> SEQUENCE: 23

Val Val Ala Ser Gln Leu Arg Ala Asn Ile Ser His Lys Asp Met Gln
1               5                   10                  15

Leu Gly Ala

<210> SEQ ID NO 24
<211> LENGTH: 12
<212> TYPE: PRT
<213> ORGANISM: Artificial Sequence
<220> FEATURE:
<223> OTHER INFORMATION: Variotope
```

```
<400> SEQUENCE: 24

Ala Asn Ile Ser His Lys Asp Met Gln Leu Gly Thr
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Variotope

<400> SEQUENCE: 25

Ala Asn Ile Ser His Lys Asp Met Gln Leu Gly Gln
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Variotope

<400> SEQUENCE: 26

Ala Asn Ile Ser His Lys Asp Met Gln Leu Gly Tyr
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Variotope

<400> SEQUENCE: 27

Ala Asn Ile Ser His Lys Asp Met Gln Leu Gly Met
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Variotope

<400> SEQUENCE: 28

Ala Asn Ile Ser His Lys Asp Met Gln Leu Gly Gly
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Variotope

<400> SEQUENCE: 29

Ala Asn Ile Ser His Lys Asp Met Gln Leu Gly Val
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Variotope
```

<400> SEQUENCE: 30

Ala Asn Ile Ser His Lys Asp Met Gln Leu Gly Lys
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Variotope

<400> SEQUENCE: 31

Ala Asn Ile Ser His Lys Asp Met Gln Leu Gly Ser
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Variotope

<400> SEQUENCE: 32

Ala Asn Ile Ser His Lys Asp Met Gln Leu Gly His
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Variotope

<400> SEQUENCE: 33

Ala Asn Ile Ser His Lys Asp Met Gln Leu Gly Asn
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Variotope

<400> SEQUENCE: 34

Ala Asn Ile Ser His Lys Asp Met Gln Leu Gly Leu
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Variotope

<400> SEQUENCE: 35

Ala Asn Ile Ser His Lys Asp Met Gln Leu Gly Trp
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Variotope

```
<400> SEQUENCE: 36

Ala Asn Ile Ser His Lys Asp Met Gln Leu Gly Phe
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Variotope

<400> SEQUENCE: 37

Ala Asn Ile Ser His Lys Asp Met Gln Leu Gly Pro
1               5                   10

<210> SEQ ID NO 38
<211> LENGTH: 12
<212> TYPE: PRT
<213> ORGANISM: Artificial Sequence
<220> FEATURE:
<223> OTHER INFORMATION: Variotope

<400> SEQUENCE: 38

Ala Asn Ile Ser His Lys Asp Met Gln Leu Gly Asp
1               5                   10

<210> SEQ ID NO 39
<211> LENGTH: 12
<212> TYPE: PRT
<213> ORGANISM: Artificial Sequence
<220> FEATURE:
<223> OTHER INFORMATION: Variotope

<400> SEQUENCE: 39

Ala Asn Ile Ser Thr Lys Asp Met Gln Leu Gly Arg
1               5                   10

<210> SEQ ID NO 40
<211> LENGTH: 12
<212> TYPE: PRT
<213> ORGANISM: Artificial Sequence
<220> FEATURE:
<223> OTHER INFORMATION: Variotope

<400> SEQUENCE: 40

Ala Asn Ile Ser Gln Lys Asp Met Gln Leu Gly Arg
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Variotope

<400> SEQUENCE: 41

Ala Asn Ile Ser Glu Lys Asp Met Gln Leu Gly Arg
1               5                   10

<210> SEQ ID NO 42
<211> LENGTH: 12
<212> TYPE: PRT
<213> ORGANISM: Artificial Sequence
<220> FEATURE:
<223> OTHER INFORMATION: Variotope
```

<400> SEQUENCE: 42

Ala Asn Ile Ser Ser Lys Asp Met Gln Leu Gly Arg
1               5                   10

<210> SEQ ID NO 43
<211> LENGTH: 12
<212> TYPE: PRT
<213> ORGANISM: Artificial Sequence
<220> FEATURE:
<223> OTHER INFORMATION: Variotope

<400> SEQUENCE: 43

Ala Asn Ile Ser Lys Lys Asp Met Gln Leu Gly Arg
1               5                   10

<210> SEQ ID NO 44
<211> LENGTH: 12
<212> TYPE: PRT
<213> ORGANISM: Artificial Sequence
<220> FEATURE:
<223> OTHER INFORMATION: Variotope

<400> SEQUENCE: 44

Ala Asn Ile Ser Asn Lys Asp Met Gln Leu Gly Arg
1               5                   10

<210> SEQ ID NO 45
<211> LENGTH: 12
<212> TYPE: PRT
<213> ORGANISM: Artificial Sequence
<220> FEATURE:
<223> OTHER INFORMATION: Variotope

<400> SEQUENCE: 45

Ala Asn Ile Ser Ile Lys Asp Met Gln Leu Gly Arg
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Variotope

<400> SEQUENCE: 46

Ala Asn Ile Ser Arg Lys Asp Met Gln Leu Gly Arg
1               5                   10

<210> SEQ ID NO 47
<211> LENGTH: 12
<212> TYPE: PRT
<213> ORGANISM: Artificial Sequence
<220> FEATURE:
<223> OTHER INFORMATION: Variotope

<400> SEQUENCE: 47

Ala Asn Ile Ser Met Lys Asp Met Gln Leu Gly Arg
1               5                   10

<210> SEQ ID NO 48
<211> LENGTH: 12
<212> TYPE: PRT
<213> ORGANISM: Artificial Sequence
<220> FEATURE:
<223> OTHER INFORMATION: Variotope

```
<400> SEQUENCE: 48

Ala Asn Ile Ser Val Lys Asp Met Gln Leu Gly Arg
1               5                   10

<210> SEQ ID NO 49
<211> LENGTH: 12
<212> TYPE: PRT
<213> ORGANISM: Artificial Sequence
<220> FEATURE:
<223> OTHER INFORMATION: Variotope

<400> SEQUENCE: 49

Ala Asn Ile Ser Tyr Lys Asp Met Gln Leu Gly Arg
1               5                   10

<210> SEQ ID NO 50
<211> LENGTH: 12
<212> TYPE: PRT
<213> ORGANISM: Artificial Sequence
<220> FEATURE:
<223> OTHER INFORMATION: Variotope

<400> SEQUENCE: 50

Ala Asn Ile Ser Leu Lys Asp Met Gln Leu Gly Arg
1               5                   10

<210> SEQ ID NO 51
<211> LENGTH: 12
<212> TYPE: PRT
<213> ORGANISM: Artificial Sequence
<220> FEATURE:
<223> OTHER INFORMATION: Variotope

<400> SEQUENCE: 51

Ala Asn Ile Ser Trp Lys Asp Met Gln Leu Gly Arg
1               5                   10

<210> SEQ ID NO 52
<211> LENGTH: 12
<212> TYPE: PRT
<213> ORGANISM: Artificial Sequence
<220> FEATURE:
<223> OTHER INFORMATION: Variotope

<400> SEQUENCE: 52

Ala Asn Ile Ser Gly Lys Asp Met Gln Leu Gly Arg
1               5                   10

<210> SEQ ID NO 53
<211> LENGTH: 12
<212> TYPE: PRT
<213> ORGANISM: Artificial Sequence
<220> FEATURE:
<223> OTHER INFORMATION: Variotope

<400> SEQUENCE: 53

Ala Asn Ile Ser Pro Lys Asp Met Gln Leu Gly Arg
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Variotope
```

<400> SEQUENCE: 54

Ala Asn Ile Ser Phe Lys Asp Met Gln Leu Gly Arg
1               5                   10

<210> SEQ ID NO 55
<211> LENGTH: 12
<212> TYPE: PRT
<213> ORGANISM: Artificial Sequence
<220> FEATURE:
<223> OTHER INFORMATION: Variotope

<400> SEQUENCE: 55

Ala Asn Ile Ser Asp Lys Asp Met Gln Leu Gly Arg
1               5                   10

<210> SEQ ID NO 56
<211> LENGTH: 12
<212> TYPE: PRT
<213> ORGANISM: Artificial Sequence
<220> FEATURE:
<223> OTHER INFORMATION: Variotope

<400> SEQUENCE: 56

Ala Asn Ile Ser His Lys Asp Val Gln Leu Gly Arg
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Variotope

<400> SEQUENCE: 57

Ala Asn Ile Ser His Lys Asp Thr Gln Leu Gly Arg
1               5                   10

<210> SEQ ID NO 58
<211> LENGTH: 12
<212> TYPE: PRT
<213> ORGANISM: Artificial Sequence
<220> FEATURE:
<223> OTHER INFORMATION: Variotope

<400> SEQUENCE: 58

Ala Asn Ile Ser His Lys Asp Tyr Gln Leu Gly Arg
1               5                   10

<210> SEQ ID NO 59
<211> LENGTH: 12
<212> TYPE: PRT
<213> ORGANISM: Artificial Sequence
<220> FEATURE:
<223> OTHER INFORMATION: Variotope

<400> SEQUENCE: 59

Ala Asn Ile Ser His Lys Asp Leu Gln Leu Gly Arg
1               5                   10

<210> SEQ ID NO 60
<211> LENGTH: 12
<212> TYPE: PRT
<213> ORGANISM: Artificial Sequence
<220> FEATURE:
<223> OTHER INFORMATION: Variotope

<400> SEQUENCE: 60

Ala Asn Ile Ser His Lys Asp Lys Gln Leu Gly Arg
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Variotope

<400> SEQUENCE: 61

Ala Asn Ile Ser His Lys Asp His Gln Leu Gly Arg
1               5                   10

<210> SEQ ID NO 62
<211> LENGTH: 12
<212> TYPE: PRT
<213> ORGANISM: Artificial Sequence
<220> FEATURE:
<223> OTHER INFORMATION: Variotope

<400> SEQUENCE: 62

Ala Asn Ile Ser His Lys Asp Arg Gln Leu Gly Arg
1               5                   10

<210> SEQ ID NO 63
<211> LENGTH: 12
<212> TYPE: PRT
<213> ORGANISM: Artificial Sequence
<220> FEATURE:
<223> OTHER INFORMATION: Variotope

<400> SEQUENCE: 63

Ala Asn Ile Ser His Lys Asp Trp Gln Leu Gly Arg
1               5                   10

<210> SEQ ID NO 64
<211> LENGTH: 12
<212> TYPE: PRT
<213> ORGANISM: Artificial Sequence
<220> FEATURE:
<223> OTHER INFORMATION: Variotope

<400> SEQUENCE: 64

Ala Asn Ile Ser His Lys Asp Ser Gln Leu Gly Arg
1               5                   10

<210> SEQ ID NO 65
<211> LENGTH: 12
<212> TYPE: PRT
<213> ORGANISM: Artificial Sequence
<220> FEATURE:
<223> OTHER INFORMATION: Variotope

<400> SEQUENCE: 65

Ala Asn Ile Ser His Lys Asp Phe Gln Leu Gly Arg
1               5                   10

<210> SEQ ID NO 66
<211> LENGTH: 12
<212> TYPE: PRT
<213> ORGANISM: Artificial Sequence
<220> FEATURE:
<223> OTHER INFORMATION: Variotope

```
<400> SEQUENCE: 66

Ala Asn Ile Ser His Lys Asp Asn Gln Leu Gly Arg
1               5                   10

<210> SEQ ID NO 67
<211> LENGTH: 12
<212> TYPE: PRT
<213> ORGANISM: Artificial Sequence
<220> FEATURE:
<223> OTHER INFORMATION: Variotope

<400> SEQUENCE: 67

Ala Asn Ile Ser His Lys Asp Pro Gln Leu Gly Arg
1               5                   10

<210> SEQ ID NO 68
<211> LENGTH: 12
<212> TYPE: PRT
<213> ORGANISM: Artificial Sequence
<220> FEATURE:
<223> OTHER INFORMATION: Variotope

<400> SEQUENCE: 68

Ala Asn Ile Ser His Lys Asp Gly Gln Leu Gly Arg
1               5                   10

<210> SEQ ID NO 69
<211> LENGTH: 12
<212> TYPE: PRT
<213> ORGANISM: Artificial Sequence
<220> FEATURE:
<223> OTHER INFORMATION: Variotope

<400> SEQUENCE: 69

Ala Asn Ile Ser His Lys Asp Asp Gln Leu Gly Arg
1               5                   10

<210> SEQ ID NO 70
<211> LENGTH: 12
<212> TYPE: PRT
<213> ORGANISM: Artificial Sequence
<220> FEATURE:
<223> OTHER INFORMATION: Variotope

<400> SEQUENCE: 70

Ala Asn Ile Ser Thr Lys Asp Met Gln Leu Gly Ala
1               5                   10

<210> SEQ ID NO 71
<211> LENGTH: 12
<212> TYPE: PRT
<213> ORGANISM: Artificial Sequence
<220> FEATURE:
<223> OTHER INFORMATION: Variotope

<400> SEQUENCE: 71

Ala Asn Ile Ser Thr Lys Asp Met Gln Leu Gly Gln
1               5                   10

<210> SEQ ID NO 72
<211> LENGTH: 12
<212> TYPE: PRT
<213> ORGANISM: Artificial Sequence
<220> FEATURE:
<223> OTHER INFORMATION: Variotope
```

```
<400> SEQUENCE: 72

Ala Asn Ile Ser Thr Lys Asp Met Gln Leu Gly Ser
1               5                   10

<210> SEQ ID NO 73
<211> LENGTH: 12
<212> TYPE: PRT
<213> ORGANISM: Artificial Sequence
<220> FEATURE:
<223> OTHER INFORMATION: Variotope

<400> SEQUENCE: 73

Ala Asn Ile Ser Thr Lys Asp Met Gln Leu Gly Met
1               5                   10

<210> SEQ ID NO 74
<211> LENGTH: 12
<212> TYPE: PRT
<213> ORGANISM: Artificial Sequence
<220> FEATURE:
<223> OTHER INFORMATION: Variotope

<400> SEQUENCE: 74

Ala Asn Ile Ser Met Lys Asp Met Gln Leu Gly Asn
1               5                   10

<210> SEQ ID NO 75
<211> LENGTH: 12
<212> TYPE: PRT
<213> ORGANISM: Artificial Sequence
<220> FEATURE:
<223> OTHER INFORMATION: Variotope

<400> SEQUENCE: 75

Ala Asn Ile Ser Thr Lys Asp Lys Gln Leu Gly Met
1               5                   10

<210> SEQ ID NO 76
<211> LENGTH: 12
<212> TYPE: PRT
<213> ORGANISM: Artificial Sequence
<220> FEATURE:
<223> OTHER INFORMATION: Variotope

<400> SEQUENCE: 76

Ala Asn Ile Ser Thr Lys Asp Met Gln Leu Gly His
1               5                   10

<210> SEQ ID NO 77
<211> LENGTH: 12
<212> TYPE: PRT
<213> ORGANISM: Artificial Sequence
<220> FEATURE:
<223> OTHER INFORMATION: Variotope

<400> SEQUENCE: 77

Ala Asn Ile Ser Ala Lys Asp Met Gln Leu Gly Ala
1               5                   10

<210> SEQ ID NO 78
<211> LENGTH: 12
<212> TYPE: PRT
<213> ORGANISM: Artificial Sequence
<220> FEATURE:
<223> OTHER INFORMATION: Variotope
```

-continued

```
<400> SEQUENCE: 78

Ala Asn Ile Ser Met Lys Asp Met Gln Leu Gly Ala
1               5                   10

<210> SEQ ID NO 79
<211> LENGTH: 12
<212> TYPE: PRT
<213> ORGANISM: Artificial Sequence
<220> FEATURE:
<223> OTHER INFORMATION: Variotope

<400> SEQUENCE: 79

Ala Asn Ile Ser Thr Lys Asp Lys Gln Leu Gly Ala
1               5                   10

<210> SEQ ID NO 80
<211> LENGTH: 12
<212> TYPE: PRT
<213> ORGANISM: Artificial Sequence
<220> FEATURE:
<223> OTHER INFORMATION: Variotope

<400> SEQUENCE: 80

Ala Asn Ile Ser Thr Lys Asp Ala Gln Leu Gly Ala
1               5                   10

<210> SEQ ID NO 81
<211> LENGTH: 12
<212> TYPE: PRT
<213> ORGANISM: Artificial Sequence
<220> FEATURE:
<223> OTHER INFORMATION: Variotope

<400> SEQUENCE: 81

Ala Asn Ile Ser Met Lys Asp Met Gln Leu Gly Ser
1               5                   10

<210> SEQ ID NO 82
<211> LENGTH: 12
<212> TYPE: PRT
<213> ORGANISM: Artificial Sequence
<220> FEATURE:
<223> OTHER INFORMATION: Variotope

<400> SEQUENCE: 82

Ala Asn Ile Ser Thr Lys Asp Val Gln Leu Gly Ala
1               5                   10

<210> SEQ ID NO 83
<211> LENGTH: 12
<212> TYPE: PRT
<213> ORGANISM: Artificial Sequence
<220> FEATURE:
<223> OTHER INFORMATION: Variotope

<400> SEQUENCE: 83

Ala Asn Ile Ser Thr Lys Asp Met Gln Leu Gly Asn
1               5                   10

<210> SEQ ID NO 84
<211> LENGTH: 12
<212> TYPE: PRT
<213> ORGANISM: Artificial Sequence
<220> FEATURE:
<223> OTHER INFORMATION: Variotope
```

```
<400> SEQUENCE: 84

Ala Asn Ile Ser Thr Lys Asp Met Gln Leu Gly Lys
1               5                   10

<210> SEQ ID NO 85
<211> LENGTH: 12
<212> TYPE: PRT
<213> ORGANISM: Artificial Sequence
<220> FEATURE:
<223> OTHER INFORMATION: Variotope

<400> SEQUENCE: 85

Ala Asn Ile Ser Met Lys Asp Met Gln Leu Gly Met
1               5                   10

<210> SEQ ID NO 86
<211> LENGTH: 12
<212> TYPE: PRT
<213> ORGANISM: Artificial Sequence
<220> FEATURE:
<223> OTHER INFORMATION: Variotope

<400> SEQUENCE: 86

Ala Asn Ile Ser Thr Lys Asp Met Gln Leu Gly Thr
1               5                   10

<210> SEQ ID NO 87
<211> LENGTH: 12
<212> TYPE: PRT
<213> ORGANISM: Artificial Sequence
<220> FEATURE:
<223> OTHER INFORMATION: Variotope

<400> SEQUENCE: 87

Ala Asn Ile Ser His Lys Asp Lys Gln Leu Gly Lys
1               5                   10

<210> SEQ ID NO 88
<211> LENGTH: 12
<212> TYPE: PRT
<213> ORGANISM: Artificial Sequence
<220> FEATURE:
<223> OTHER INFORMATION: Variotope

<400> SEQUENCE: 88

Ala Asn Ile Ser Met Lys Asp Met Gln Leu Gly His
1               5                   10

<210> SEQ ID NO 89
<211> LENGTH: 12
<212> TYPE: PRT
<213> ORGANISM: Artificial Sequence
<220> FEATURE:
<223> OTHER INFORMATION: Variotope

<400> SEQUENCE: 89

Ala Asn Ile Ser Ala Lys Asp Ala Gln Leu Gly Ala
1               5                   10

<210> SEQ ID NO 90
<211> LENGTH: 12
<212> TYPE: PRT
<213> ORGANISM: Artificial Sequence
<220> FEATURE:
<223> OTHER INFORMATION: Variotope
```

-continued

<400> SEQUENCE: 90

Ala Asn Ile Ser Met Lys Asp Lys Gln Leu Gly Lys
1               5                   10

<210> SEQ ID NO 91
<211> LENGTH: 12
<212> TYPE: PRT
<213> ORGANISM: Artificial Sequence
<220> FEATURE:
<223> OTHER INFORMATION: Variotope

<400> SEQUENCE: 91

Ala Asn Ile Ser His Lys Asp Ser Gln Leu Gly Lys
1               5                   10

<210> SEQ ID NO 92
<211> LENGTH: 12
<212> TYPE: PRT
<213> ORGANISM: Artificial Sequence
<220> FEATURE:
<223> OTHER INFORMATION: Variotope

<400> SEQUENCE: 92

Ala Asn Ile Ser Met Lys Asp Met Gln Leu Gly Phe
1               5                   10

<210> SEQ ID NO 93
<211> LENGTH: 12
<212> TYPE: PRT
<213> ORGANISM: Artificial Sequence
<220> FEATURE:
<223> OTHER INFORMATION: Variotope

<400> SEQUENCE: 93

Ala Asn Ile Ser Ile Lys Asp Met Gln Leu Gly Ala
1               5                   10

<210> SEQ ID NO 94
<211> LENGTH: 12
<212> TYPE: PRT
<213> ORGANISM: Artificial Sequence
<220> FEATURE:
<223> OTHER INFORMATION: Variotope

<400> SEQUENCE: 94

Ala Asn Ile Ser Met Lys Asp Met Gln Leu Gly Lys
1               5                   10

<210> SEQ ID NO 95
<211> LENGTH: 12
<212> TYPE: PRT
<213> ORGANISM: Artificial Sequence
<220> FEATURE:
<223> OTHER INFORMATION: Variotope

<400> SEQUENCE: 95

Ala Asn Ile Ser Leu Lys Asp Met Gln Leu Gly Ala
1               5                   10

<210> SEQ ID NO 96
<211> LENGTH: 12
<212> TYPE: PRT
<213> ORGANISM: Artificial Sequence
<220> FEATURE:
<223> OTHER INFORMATION: Variotope

```
<400> SEQUENCE: 96

Ala Asn Ile Ser His Lys Asp Lys Gln Leu Gly Phe
1               5                   10

<210> SEQ ID NO 97
<211> LENGTH: 12
<212> TYPE: PRT
<213> ORGANISM: Artificial Sequence
<220> FEATURE:
<223> OTHER INFORMATION: Variotope

<400> SEQUENCE: 97

Ala Asn Ile Ser Met Lys Asp Lys Gln Leu Gly Phe
1               5                   10

<210> SEQ ID NO 98
<211> LENGTH: 12
<212> TYPE: PRT
<213> ORGANISM: Artificial Sequence
<220> FEATURE:
<223> OTHER INFORMATION: Variotope

<400> SEQUENCE: 98

Ala Asn Ile Ser Ile Lys Asp Met Gln Leu Gly Lys
1               5                   10

<210> SEQ ID NO 99
<211> LENGTH: 8
<212> TYPE: PRT
<213> ORGANISM: Artificial Sequence
<220> FEATURE:
<223> OTHER INFORMATION: Variotope
<220> FEATURE:
<221> NAME/KEY: MISC_FEATURE
<222> LOCATION: (1)..(1)
<223> OTHER INFORMATION: X = SEQ ID No. 100 or an N-terminal truncated
      fragment thereof consisting of 1 to 6 amino acid residues
<220> FEATURE:
<221> NAME/KEY: MISC_FEATURE
<222> LOCATION: (4)..(4)
<223> OTHER INFORMATION: X = an amino acid residue selected from the
      group consisting of alanine, arginine, histidine, isoleucine,
      leucine, lysine, methionine, threonine, tyrosine and valine
<220> FEATURE:
<221> NAME/KEY: MISC_FEATURE
<222> LOCATION: (8)..(8)
<223> OTHER INFORMATION: X = an amino acid residue selected from the
      group consisting of alanine, asparagine, glutamine, glycine,
      histidine, isoleucine, leucine, lysine, methionine, serine,
      threonine, tyrosine and valine

<400> SEQUENCE: 99

Xaa Lys Asp Xaa Gln Leu Gly Xaa
1               5

<210> SEQ ID NO 100
<211> LENGTH: 6
<212> TYPE: PRT
<213> ORGANISM: Artificial Sequence
<220> FEATURE:
<223> OTHER INFORMATION: Variotope
<220> FEATURE:
<221> NAME/KEY: MISC_FEATURE
<222> LOCATION: (1)..(1)
<223> OTHER INFORMATION: X = VVASQLR (SEQ ID No. 101) or an N-terminal
      truncated fragment thereof consisting of 1 to 6 amino acid
      residues
```

```
<220> FEATURE:
<221> NAME/KEY: MISC_FEATURE
<222> LOCATION: (6)..(6)
<223> OTHER INFORMATION: X = an amino acid residue selected from the
      group consisting of alanine, asparagine, glutamine, glutamic acid,
      histidine, arginine, isoleucine, lysine, methionine, serine and
      threonine

<400> SEQUENCE: 100

Xaa Ala Asn Ile Ser Xaa
1               5

<210> SEQ ID NO 101
<211> LENGTH: 7
<212> TYPE: PRT
<213> ORGANISM: Homo sapiens

<400> SEQUENCE: 101

Val Val Ala Ser Gln Leu Arg
1               5

<210> SEQ ID NO 102
<211> LENGTH: 5
<212> TYPE: PRT
<213> ORGANISM: Artificial Sequence
<220> FEATURE:
<223> OTHER INFORMATION: Variotope
<220> FEATURE:
<221> NAME/KEY: MISC_FEATURE
<222> LOCATION: (5)..(5)
<223> OTHER INFORMATION: X = an amino acid residue selected from the
      group consisting of alanine, asparagine, glutamine, glutamic acid,
      histidine, arginine, isoleucine, lysine, methionine, serine and
      threonine

<400> SEQUENCE: 102

Ala Asn Ile Ser Xaa
1               5

<210> SEQ ID NO 103
<211> LENGTH: 4
<212> TYPE: PRT
<213> ORGANISM: Artificial Sequence
<220> FEATURE:
<223> OTHER INFORMATION: Variotope
<220> FEATURE:
<221> NAME/KEY: MISC_FEATURE
<222> LOCATION: (4)..(4)
<223> OTHER INFORMATION: X = an amino acid residue selected from the
      group consisting of alanine, asparagine, glutamine, glutamic acid,
      histidine, arginine, isoleucine, lysine, methionine, serine and
      threonine

<400> SEQUENCE: 103

Asn Ile Ser Xaa
1

<210> SEQ ID NO 104
<211> LENGTH: 12
<212> TYPE: PRT
<213> ORGANISM: Artificial Sequence
<220> FEATURE:
<223> OTHER INFORMATION: Variotope
<220> FEATURE:
<221> NAME/KEY: MISC_FEATURE
<222> LOCATION: (5)..(5)
<223> OTHER INFORMATION: X = an amino acid residue selected from the
      group consisting of alanine, asparagine, glutamine, glutamic acid,
      histidine, arginine, isoleucine, lysine, methionine, serine and
      threonine
```

```
<220> FEATURE:
<221> NAME/KEY: MISC_FEATURE
<222> LOCATION: (8)..(8)
<223> OTHER INFORMATION: X = an amino acid residue selected from the
      group consisting of alanine, arginine, histidine, isoleucine,
      leucine, lysine, methionine, threonine, tyrosine and valine
<220> FEATURE:
<221> NAME/KEY: MISC_FEATURE
<222> LOCATION: (12)..(12)
<223> OTHER INFORMATION: X = an amino acid residue selected from the
      group consisting of alanine, asparagine, glutamine, glycine,
      histidine, iso-leucine, leucine, lysine, methionine, serine,
      threonine, tyro-sine and valine

<400> SEQUENCE: 104

Ala Asn Ile Ser Xaa Lys Asp Xaa Gln Leu Gly Xaa
1               5                   10

<210> SEQ ID NO 105
<211> LENGTH: 11
<212> TYPE: PRT
<213> ORGANISM: Artificial Sequence
<220> FEATURE:
<223> OTHER INFORMATION: Variotope
<220> FEATURE:
<221> NAME/KEY: MISC_FEATURE
<222> LOCATION: (4)..(4)
<223> OTHER INFORMATION: X = an amino acid residue selected from the
      group consisting of alanine, asparagine, glutamine, glutamic acid,
      histidine, arginine, isoleucine, lysine, methionine, serine and
      threonine
<220> FEATURE:
<221> NAME/KEY: MISC_FEATURE
<222> LOCATION: (7)..(7)
<223> OTHER INFORMATION: X = an amino acid residue selected from the
      group consisting of alanine, arginine, histidine, isoleucine,
      leucine, lysine, methionine, threonine, tyrosine and valine
<220> FEATURE:
<221> NAME/KEY: MISC_FEATURE
<222> LOCATION: (11)..(11)
<223> OTHER INFORMATION: X = an amino acid residue selected from the
      group consisting of alanine, asparagine, glutamine, glycine,
      histidine, iso-leucine, leucine, lysine, methionine, serine,
      threonine, tyro-sine and valine

<400> SEQUENCE: 105

Asn Ile Ser Xaa Lys Asp Xaa Gln Leu Gly Xaa
1               5                   10

<210> SEQ ID NO 106
<211> LENGTH: 10
<212> TYPE: PRT
<213> ORGANISM: Artificial Sequence
<220> FEATURE:
<223> OTHER INFORMATION: Variotope
<220> FEATURE:
<221> NAME/KEY: MISC_FEATURE
<222> LOCATION: (3)..(3)
<223> OTHER INFORMATION: X = an amino acid residue selected from the
      group consisting of alanine, asparagine, glutamine, glutamic acid,
      histidine, arginine, isoleucine, lysine, methionine, serine and
      threonine
<220> FEATURE:
<221> NAME/KEY: MISC_FEATURE
<222> LOCATION: (6)..(6)
<223> OTHER INFORMATION: X = an amino acid residue selected from the
      group consisting of alanine, arginine, histidine, isoleucine,
      leucine, lysine, methionine, threonine, tyrosine and valine
<220> FEATURE:
<221> NAME/KEY: MISC_FEATURE
<222> LOCATION: (10)..(10)
<223> OTHER INFORMATION: X = an amino acid residue selected from the
      group consisting of alanine, asparagine, glutamine, glycine,
      histidine, iso-leucine, leucine, lysine, methionine, serine,
      threonine, tyro-sine and valine
```

```
<400> SEQUENCE: 106

Ile Ser Xaa Lys Asp Xaa Gln Leu Gly Xaa
1               5                   10

<210> SEQ ID NO 107
<211> LENGTH: 9
<212> TYPE: PRT
<213> ORGANISM: Artificial Sequence
<220> FEATURE:
<223> OTHER INFORMATION: Variotope
<220> FEATURE:
<221> NAME/KEY: MISC_FEATURE
<222> LOCATION: (2)..(2)
<223> OTHER INFORMATION: X = an amino acid residue selected from the
      group consisting of alanine, asparagine, glutamine, glutamic acid,
      histidine, arginine, isoleucine, lysine, methionine, serine and
      threonine
<220> FEATURE:
<221> NAME/KEY: MISC_FEATURE
<222> LOCATION: (5)..(5)
<223> OTHER INFORMATION: X = an amino acid residue selected from the
      group consisting of alanine, arginine, histidine, isoleucine,
      leucine, lysine, methionine, threonine, tyrosine and valine
<220> FEATURE:
<221> NAME/KEY: MISC_FEATURE
<222> LOCATION: (9)..(9)
<223> OTHER INFORMATION: X = an amino acid residue selected from the
      group consisting of alanine, asparagine, glutamine, glycine,
      histidine, iso-leucine, leucine, lysine, methionine, serine,
      threonine, tyro-sine and valine

<400> SEQUENCE: 107

Ser Xaa Lys Asp Xaa Gln Leu Gly Xaa
1               5

<210> SEQ ID NO 108
<211> LENGTH: 8
<212> TYPE: PRT
<213> ORGANISM: Artificial Sequence
<220> FEATURE:
<223> OTHER INFORMATION: Variotope
<220> FEATURE:
<221> NAME/KEY: MISC_FEATURE
<222> LOCATION: (1)..(1)
<223> OTHER INFORMATION: X = an amino acid residue selected from the
      group consisting of alanine, asparagine, glutamine, glutamic acid,
      histidine, arginine, isoleucine, lysine, methionine, serine and
      threonine
<220> FEATURE:
<221> NAME/KEY: MISC_FEATURE
<222> LOCATION: (4)..(4)
<223> OTHER INFORMATION: X = an amino acid residue selected from the
      group consisting of alanine, arginine, histidine, isoleucine,
      leucine, lysine, methionine, threonine, tyrosine and valine
<220> FEATURE:
<221> NAME/KEY: MISC_FEATURE
<222> LOCATION: (8)..(8)
<223> OTHER INFORMATION: X = an amino acid residue selected from the
      group consisting of alanine, asparagine, glutamine, glycine,
      histidine, iso-leucine, leucine, lysine, methionine, serine,
      threonine, tyro-sine and valine

<400> SEQUENCE: 108

Xaa Lys Asp Xaa Gln Leu Gly Xaa
1               5

<210> SEQ ID NO 109
<211> LENGTH: 6
<212> TYPE: PRT
<213> ORGANISM: Homo sapiens
```

```
<400> SEQUENCE: 109

Val Ala Ser Gln Leu Arg
1               5

<210> SEQ ID NO 110
<211> LENGTH: 5
<212> TYPE: PRT
<213> ORGANISM: Homo sapiens

<400> SEQUENCE: 110

Ala Ser Gln Leu Arg
1               5

<210> SEQ ID NO 111
<211> LENGTH: 4
<212> TYPE: PRT
<213> ORGANISM: Homo sapiens

<400> SEQUENCE: 111

Ser Gln Leu Arg
1

<210> SEQ ID NO 112
<211> LENGTH: 19
<212> TYPE: PRT
<213> ORGANISM: Artificial Sequence
<220> FEATURE:
<223> OTHER INFORMATION: Variotope
<220> FEATURE:
<221> NAME/KEY: MISC_FEATURE
<222> LOCATION: (12)..(12)
<223> OTHER INFORMATION: X = an amino acid residue selected from the
      group consisting of alanine, asparagine, glutamine, glutamic acid,
      histidine, arginine, isoleucine, lysine, methionine, serine and
      threonine
<220> FEATURE:
<221> NAME/KEY: MISC_FEATURE
<222> LOCATION: (15)..(15)
<223> OTHER INFORMATION: X = an amino acid residue selected from the
      group consisting of alanine, arginine, histidine, isoleucine,
      leucine, lysine, methionine, threonine, tyrosine and valine
<220> FEATURE:
<221> NAME/KEY: MISC_FEATURE
<222> LOCATION: (19)..(19)
<223> OTHER INFORMATION: X = an amino acid residue selected from the
      group consisting of alanine, asparagine, glutamine, glycine,
      histidine, isoleucine, leucine, lysine, methionine, serine,
      threonine, tyrosine and valine

<400> SEQUENCE: 112

Val Val Ala Ser Gln Leu Arg Ala Asn Ile Ser Xaa Lys Asp Xaa Gln
1               5                   10                  15

Leu Gly Xaa

<210> SEQ ID NO 113
<211> LENGTH: 18
<212> TYPE: PRT
<213> ORGANISM: Artificial Sequence
<220> FEATURE:
<223> OTHER INFORMATION: Variotope
<220> FEATURE:
<221> NAME/KEY: MISC_FEATURE
<222> LOCATION: (11)..(11)
<223> OTHER INFORMATION: X = an amino acid residue selected from the
      group consisting of alanine, asparagine, glutamine, glutamic acid,
      histidine, arginine, isoleucine, lysine, methionine, serine and
      threonine
```

```
<220> FEATURE:
<221> NAME/KEY: MISC_FEATURE
<222> LOCATION: (14)..(14)
<223> OTHER INFORMATION: X = an amino acid residue selected from the
      group consisting of alanine, arginine, histidine, isoleucine,
      leucine, lysine, methionine, threonine, tyrosine and valine
<220> FEATURE:
<221> NAME/KEY: MISC_FEATURE
<222> LOCATION: (18)..(18)
<223> OTHER INFORMATION: X = an amino acid residue selected from the
      group consisting of alanine, asparagine, glutamine, glycine,
      histidine, iso-leucine, leucine, lysine, methionine, serine,
      threonine, tyro-sine and valine

<400> SEQUENCE: 113

Val Ala Ser Gln Leu Arg Ala Asn Ile Ser Xaa Lys Asp Xaa Gln Leu
1               5                   10                  15

Gly Xaa

<210> SEQ ID NO 114
<211> LENGTH: 17
<212> TYPE: PRT
<213> ORGANISM: Artificial Sequence
<220> FEATURE:
<223> OTHER INFORMATION: Variotope
<220> FEATURE:
<221> NAME/KEY: MISC_FEATURE
<222> LOCATION: (10)..(10)
<223> OTHER INFORMATION: X = an amino acid residue selected from the
      group consisting of alanine, asparagine, glutamine, glutamic acid,
      histidine, arginine, isoleucine, lysine, methionine, serine and
      threonine
<220> FEATURE:
<221> NAME/KEY: MISC_FEATURE
<222> LOCATION: (13)..(13)
<223> OTHER INFORMATION: X = an amino acid residue selected from the
      group consisting of alanine, arginine, histidine, isoleucine,
      leucine, lysine, methionine, threonine, tyrosine and valine
<220> FEATURE:
<221> NAME/KEY: MISC_FEATURE
<222> LOCATION: (17)..(17)
<223> OTHER INFORMATION: X = an amino acid residue selected from the
      group consisting of alanine, asparagine, glutamine, glycine,
      histidine, iso-leucine, leucine, lysine, methionine, serine,
      threonine, tyro-sine and valine

<400> SEQUENCE: 114

Ala Ser Gln Leu Arg Ala Asn Ile Ser Xaa Lys Asp Xaa Gln Leu Gly
1               5                   10                  15

Xaa

<210> SEQ ID NO 115
<211> LENGTH: 16
<212> TYPE: PRT
<213> ORGANISM: Artificial Sequence
<220> FEATURE:
<223> OTHER INFORMATION: Variotope
<220> FEATURE:
<221> NAME/KEY: MISC_FEATURE
<222> LOCATION: (9)..(9)
<223> OTHER INFORMATION: X = an amino acid residue selected from the
      group consisting of alanine, asparagine, glutamine, glutamic acid,
      histidine, arginine, isoleucine, lysine, methionine, serine and
      threonine
<220> FEATURE:
<221> NAME/KEY: MISC_FEATURE
<222> LOCATION: (12)..(12)
<223> OTHER INFORMATION: X = an amino acid residue selected from the
      group consisting of alanine, arginine, histidine, isoleucine,
      leucine, lysine, methionine, threonine, tyrosine and valine
```

```
<220> FEATURE:
<221> NAME/KEY: MISC_FEATURE
<222> LOCATION: (16)..(16)
<223> OTHER INFORMATION: X = an amino acid residue selected from the
      group consisting of alanine, asparagine, glutamine, glycine,
      histidine, isoleucine, leucine, lysine, methionine, serine,
      threonine, tyrosine and valine

<400> SEQUENCE: 115

Ser Gln Leu Arg Ala Asn Ile Ser Xaa Lys Asp Xaa Gln Leu Gly Xaa
1               5                   10                  15

<210> SEQ ID NO 116
<211> LENGTH: 15
<212> TYPE: PRT
<213> ORGANISM: Artificial Sequence
<220> FEATURE:
<223> OTHER INFORMATION: Variotope
<220> FEATURE:
<221> NAME/KEY: MISC_FEATURE
<222> LOCATION: (8)..(8)
<223> OTHER INFORMATION: X = an amino acid residue selected from the
      group consisting of alanine, asparagine, glutamine, glutamic acid,
      histidine, arginine, isoleucine, lysine, methionine, serine and
      threonine
<220> FEATURE:
<221> NAME/KEY: MISC_FEATURE
<222> LOCATION: (11)..(11)
<223> OTHER INFORMATION: X = an amino acid residue selected from the
      group consisting of alanine, arginine, histidine, isoleucine,
      leucine, lysine, methionine, threonine, tyrosine and valine
<220> FEATURE:
<221> NAME/KEY: MISC_FEATURE
<222> LOCATION: (15)..(15)
<223> OTHER INFORMATION: X = an amino acid residue selected from the
      group consisting of alanine, asparagine, glutamine, glycine,
      histidine, isoleucine, leucine, lysine, methionine, serine,
      threonine, tyrosine and valine

<400> SEQUENCE: 116

Gln Leu Arg Ala Asn Ile Ser Xaa Lys Asp Xaa Gln Leu Gly Xaa
1               5                   10                  15

<210> SEQ ID NO 117
<211> LENGTH: 14
<212> TYPE: PRT
<213> ORGANISM: Artificial Sequence
<220> FEATURE:
<223> OTHER INFORMATION: Variotope
<220> FEATURE:
<221> NAME/KEY: MISC_FEATURE
<222> LOCATION: (7)..(7)
<223> OTHER INFORMATION: X = an amino acid residue selected from the
      group consisting of alanine, asparagine, glutamine, glutamic acid,
      histidine, arginine, isoleucine, lysine, methionine, serine and
      threonine
<220> FEATURE:
<221> NAME/KEY: MISC_FEATURE
<222> LOCATION: (10)..(10)
<223> OTHER INFORMATION: X = an amino acid residue selected from the
      group consisting of alanine, arginine, histidine, isoleucine,
      leucine, lysine, methionine, threonine, tyrosine and valine
<220> FEATURE:
<221> NAME/KEY: MISC_FEATURE
<222> LOCATION: (14)..(14)
<223> OTHER INFORMATION: X = an amino acid residue selected from the
      group consisting of alanine, asparagine, glutamine, glycine,
      histidine, iso-leucine, leucine, lysine, methionine, serine,
      threonine, tyro-sine and valine
```

```
<220> FEATURE:
<221> NAME/KEY: MISC_FEATURE
<222> LOCATION: (14)..(14)
<223> OTHER INFORMATION: X = an amino acid residue selected from the
      group consisting of alanine, asparagine, glutamine, glycine,
      histidine, isoleucine, leucine, lysine, methionine, serine,
      threonine, tyrosine and valine

<400> SEQUENCE: 117

Leu Arg Ala Asn Ile Ser Xaa Lys Asp Xaa Gln Leu Gly Xaa
1               5                   10

<210> SEQ ID NO 118
<211> LENGTH: 13
<212> TYPE: PRT
<213> ORGANISM: Artificial Sequence
<220> FEATURE:
<223> OTHER INFORMATION: Variotope
<220> FEATURE:
<221> NAME/KEY: MISC_FEATURE
<222> LOCATION: (6)..(6)
<223> OTHER INFORMATION: X = an amino acid residue selected from the
      group consisting of alanine, asparagine, glutamine, glutamic acid,
      histidine, arginine, isoleucine, lysine, methionine, serine and
      threonine
<220> FEATURE:
<221> NAME/KEY: MISC_FEATURE
<222> LOCATION: (9)..(9)
<223> OTHER INFORMATION: X = an amino acid residue selected from the
      group consisting of alanine, arginine, histidine, isoleucine,
      leucine, lysine, methionine, threonine, tyrosine and valine
<220> FEATURE:
<221> NAME/KEY: MISC_FEATURE
<222> LOCATION: (13)..(13)
<223> OTHER INFORMATION: X = an amino acid residue selected from the
      group consisting of alanine, asparagine, glutamine, glycine,
      histidine, isoleucine, leucine, lysine, methionine, serine,
      threonine, tyrosine and valine

<400> SEQUENCE: 118

Arg Ala Asn Ile Ser Xaa Lys Asp Xaa Gln Leu Gly Xaa
1               5                   10

<210> SEQ ID NO 119
<211> LENGTH: 12
<212> TYPE: PRT
<213> ORGANISM: Artificial Sequence
<220> FEATURE:
<223> OTHER INFORMATION: Variotope
<220> FEATURE:
<221> NAME/KEY: MISC_FEATURE
<222> LOCATION: (5)..(5)
<223> OTHER INFORMATION: X = an amino acid residue selected from the
      group consisting of alanine, asparagine, glutamine, glutamic acid,
      histidine, arginine, isoleucine, lysine, methionine, serine and
      threonine
<220> FEATURE:
<221> NAME/KEY: MISC_FEATURE
<222> LOCATION: (8)..(8)
<223> OTHER INFORMATION: X = an amino acid residue selected from the
      group consisting of alanine, arginine, histidine, isoleucine,
      leucine, lysine, methionine, threonine, tyrosine and valine

<400> SEQUENCE: 119

Ala Asn Ile Ser Xaa Lys Asp Xaa Gln Leu Gly Arg
1               5                   10

<210> SEQ ID NO 120
<211> LENGTH: 11
<212> TYPE: PRT
<213> ORGANISM: Artificial Sequence
<220> FEATURE:
<223> OTHER INFORMATION: Variotope
```

```
<220> FEATURE:
<221> NAME/KEY: MISC_FEATURE
<222> LOCATION: (4)..(4)
<223> OTHER INFORMATION: X = an amino acid residue selected from the
      group consisting of alanine, asparagine, glutamine, glutamic acid,
      histidine, arginine, isoleucine, lysine, methionine, serine and
      threonine
<220> FEATURE:
<221> NAME/KEY: MISC_FEATURE
<222> LOCATION: (7)..(7)
<223> OTHER INFORMATION: X = an amino acid residue selected from the
      group consisting of alanine, arginine, histidine, isoleucine,
      leucine, lysine, methionine, threonine, tyrosine and valine

<400> SEQUENCE: 120

Asn Ile Ser Xaa Lys Asp Xaa Gln Leu Gly Arg
1               5                   10

<210> SEQ ID NO 121
<211> LENGTH: 10
<212> TYPE: PRT
<213> ORGANISM: Artificial Sequence
<220> FEATURE:
<223> OTHER INFORMATION: Variotope
<220> FEATURE:
<221> NAME/KEY: MISC_FEATURE
<222> LOCATION: (3)..(3)
<223> OTHER INFORMATION: X = an amino acid residue selected from the
      group consisting of alanine, asparagine, glutamine, glutamic acid,
      histidine, arginine, isoleucine, lysine, methionine, serine and
      threonine
<220> FEATURE:
<221> NAME/KEY: MISC_FEATURE
<222> LOCATION: (6)..(6)
<223> OTHER INFORMATION: X = an amino acid residue selected from the
      group consisting of alanine, arginine, histidine, isoleucine,
      leucine, lysine, methionine, threonine, tyrosine and valine

<400> SEQUENCE: 121

Ile Ser Xaa Lys Asp Xaa Gln Leu Gly Arg
1               5                   10

<210> SEQ ID NO 122
<211> LENGTH: 9
<212> TYPE: PRT
<213> ORGANISM: Artificial Sequence
<220> FEATURE:
<223> OTHER INFORMATION: Variotope
<220> FEATURE:
<221> NAME/KEY: MISC_FEATURE
<222> LOCATION: (2)..(2)
<223> OTHER INFORMATION: X = an amino acid residue selected from the
      group consisting of alanine, asparagine, glutamine, glutamic acid,
      histidine, arginine, isoleucine, lysine, methionine, serine and
      threonine
<220> FEATURE:
<221> NAME/KEY: MISC_FEATURE
<222> LOCATION: (5)..(5)
<223> OTHER INFORMATION: X = an amino acid residue selected from the
      group consisting of alanine, arginine, histidine, isoleucine,
      leucine, lysine, methionine, threonine, tyrosine and valine

<400> SEQUENCE: 122

Ser Xaa Lys Asp Xaa Gln Leu Gly Arg
1               5

<210> SEQ ID NO 123
<211> LENGTH: 8
<212> TYPE: PRT
<213> ORGANISM: Artificial Sequence
<220> FEATURE:
<223> OTHER INFORMATION: Variotope
```

```
<220> FEATURE:
<221> NAME/KEY: MISC_FEATURE
<222> LOCATION: (1)..(1)
<223> OTHER INFORMATION: X = an amino acid residue selected from the
      group consisting of alanine, asparagine, glutamine, glutamic acid,
      histidine, arginine, isoleucine, lysine, methionine, serine and
      threonine
<220> FEATURE:
<221> NAME/KEY: MISC_FEATURE
<222> LOCATION: (4)..(4)
<223> OTHER INFORMATION: X = an amino acid residue selected from the
      group consisting of alanine, arginine, histidine, isoleucine,
      leucine, lysine, methionine, threonine, tyrosine and valine

<400> SEQUENCE: 123

Xaa Lys Asp Xaa Gln Leu Gly Arg
1               5

<210> SEQ ID NO 124
<211> LENGTH: 19
<212> TYPE: PRT
<213> ORGANISM: Artificial Sequence
<220> FEATURE:
<223> OTHER INFORMATION: Variotope
<220> FEATURE:
<221> NAME/KEY: MISC_FEATURE
<222> LOCATION: (12)..(12)
<223> OTHER INFORMATION: X = an amino acid residue selected from the
      group consisting of alanine, asparagine, glutamine, glutamic acid,
      histidine, arginine, isoleucine, lysine, methionine, serine and
      threonine
<220> FEATURE:
<221> NAME/KEY: MISC_FEATURE
<222> LOCATION: (15)..(15)
<223> OTHER INFORMATION: X = an amino acid residue selected from the
      group consisting of alanine, arginine, histidine, isoleucine,
      leucine, lysine, methionine, threonine, tyrosine and valine

<400> SEQUENCE: 124

Val Val Ala Ser Gln Leu Arg Ala Asn Ile Ser Xaa Lys Asp Xaa Gln
1               5                   10                  15

Leu Gly Arg

<210> SEQ ID NO 125
<211> LENGTH: 18
<212> TYPE: PRT
<213> ORGANISM: Artificial Sequence
<220> FEATURE:
<223> OTHER INFORMATION: Variotope
<220> FEATURE:
<221> NAME/KEY: MISC_FEATURE
<222> LOCATION: (11)..(11)
<223> OTHER INFORMATION: X = an amino acid residue selected from the
      group consisting of alanine, asparagine, glutamine, glutamic acid,
      histidine, arginine, isoleucine, lysine, methionine, serine and
      threonine
<220> FEATURE:
<221> NAME/KEY: MISC_FEATURE
<222> LOCATION: (14)..(14)
<223> OTHER INFORMATION: X = an amino acid residue selected from the
      group consisting of alanine, arginine, histidine, isoleucine,
      leucine, lysine, methionine, threonine, tyrosine and valine

<400> SEQUENCE: 125

Val Ala Ser Gln Leu Arg Ala Asn Ile Ser Xaa Lys Asp Xaa Gln Leu
1               5                   10                  15

Gly Arg
```

```
<210> SEQ ID NO 126
<211> LENGTH: 17
<212> TYPE: PRT
<213> ORGANISM: Artificial Sequence
<220> FEATURE:
<223> OTHER INFORMATION: Variotope
<220> FEATURE:
<221> NAME/KEY: MISC_FEATURE
<222> LOCATION: (10)..(10)
<223> OTHER INFORMATION: X = an amino acid residue selected from the
      group consisting of alanine, asparagine, glutamine, glutamic acid,
      histidine, arginine, isoleucine, lysine, methionine, serine and
      threonine
<220> FEATURE:
<221> NAME/KEY: MISC_FEATURE
<222> LOCATION: (13)..(13)
<223> OTHER INFORMATION: X = an amino acid residue selected from the
      group consisting of alanine, arginine, histidine, isoleucine,
      leucine, lysine, methionine, threonine, tyrosine and valine

<400> SEQUENCE: 126

Ala Ser Gln Leu Arg Ala Asn Ile Ser Xaa Lys Asp Xaa Gln Leu Gly
1               5                   10                  15

Arg

<210> SEQ ID NO 127
<211> LENGTH: 16
<212> TYPE: PRT
<213> ORGANISM: Artificial Sequence
<220> FEATURE:
<223> OTHER INFORMATION: Variotope
<220> FEATURE:
<221> NAME/KEY: MISC_FEATURE
<222> LOCATION: (9)..(9)
<223> OTHER INFORMATION: X = an amino acid residue selected from the
      group consisting of alanine, asparagine, glutamine, glutamic acid,
      histidine, arginine, isoleucine, lysine, methionine, serine and
      threonine
<220> FEATURE:
<221> NAME/KEY: MISC_FEATURE
<222> LOCATION: (12)..(12)
<223> OTHER INFORMATION: X = an amino acid residue selected from the
      group consisting of alanine, arginine, histidine, isoleucine,
      leucine, lysine, methionine, threonine, tyrosine and valine

<400> SEQUENCE: 127

Ser Gln Leu Arg Ala Asn Ile Ser Xaa Lys Asp Xaa Gln Leu Gly Arg
1               5                   10                  15

<210> SEQ ID NO 128
<211> LENGTH: 15
<212> TYPE: PRT
<213> ORGANISM: Artificial Sequence
<220> FEATURE:
<223> OTHER INFORMATION: Variotope
<220> FEATURE:
<221> NAME/KEY: MISC_FEATURE
<222> LOCATION: (8)..(8)
<223> OTHER INFORMATION: X = an amino acid residue selected from the
      group consisting of alanine, asparagine, glutamine, glutamic acid,
      histidine, arginine, isoleucine, lysine, methionine, serine and
      threonine
<220> FEATURE:
<221> NAME/KEY: MISC_FEATURE
<222> LOCATION: (11)..(11)
<223> OTHER INFORMATION: X = an amino acid residue selected from the
      group consisting of alanine, arginine, histidine, isoleucine,
      leucine, lysine, methionine, threonine, tyrosine and valine

<400> SEQUENCE: 128

Gln Leu Arg Ala Asn Ile Ser Xaa Lys Asp Xaa Gln Leu Gly Arg
1               5                   10                  15
```

```
<210> SEQ ID NO 129
<211> LENGTH: 14
<212> TYPE: PRT
<213> ORGANISM: Artificial Sequence
<220> FEATURE:
<223> OTHER INFORMATION: Variotope
<220> FEATURE:
<221> NAME/KEY: MISC_FEATURE
<222> LOCATION: (7)..(7)
<223> OTHER INFORMATION: X = an amino acid residue selected from the
      group consisting of alanine, asparagine, glutamine, glutamic acid,
      histidine, arginine, isoleucine, lysine, methionine, serine and
      threonine
<220> FEATURE:
<221> NAME/KEY: MISC_FEATURE
<222> LOCATION: (10)..(10)
<223> OTHER INFORMATION: X = an amino acid residue selected from the
      group consisting of alanine, arginine, histidine, isoleucine,
      leucine, lysine, methionine, threonine, tyrosine and valine

<400> SEQUENCE: 129

Leu Arg Ala Asn Ile Ser Xaa Lys Asp Xaa Gln Leu Gly Arg
1               5                   10

<210> SEQ ID NO 130
<211> LENGTH: 13
<212> TYPE: PRT
<213> ORGANISM: Artificial Sequence
<220> FEATURE:
<223> OTHER INFORMATION: Variotope
<220> FEATURE:
<221> NAME/KEY: MISC_FEATURE
<222> LOCATION: (6)..(6)
<223> OTHER INFORMATION: X = an amino acid residue selected from the
      group consisting of alanine, asparagine, glutamine, glutamic acid,
      histidine, arginine, isoleucine, lysine, methionine, serine and
      threonine
<220> FEATURE:
<221> NAME/KEY: MISC_FEATURE
<222> LOCATION: (9)..(9)
<223> OTHER INFORMATION: X = an amino acid residue selected from the
      group consisting of alanine, arginine, histidine, isoleucine,
      leucine, lysine, methionine, threonine, tyrosine and valine

<400> SEQUENCE: 130

Arg Ala Asn Ile Ser Xaa Lys Asp Xaa Gln Leu Gly Arg
1               5                   10
```

METHOD OF INHIBITING C5A

The present invention relates to a medicament to be used in the fields of medicine, immunology, and molecular biology to prevent and/or treat complement component C5a induced chronic inflammatory diseases.

The complement is a central component of the innate immune system, protecting the host from microorganisms such as viruses, bacteria, and other foreign and abnormal cells. However, inappropriate or excessive activation of the complement system can lead to destructive capabilities against the host itself. Uncontrolled complement activation is involved in a number of chronic inflammatory diseases such as Alzheimer's disease, Parkinson's disease, Huntington's disease, age-related macula degeneration, rheumatoid arthritis, systemic lupus erythematosus, antiphospholipid syndrome, asthma, vasculitis, atherosclerosis, multiple sclerosis, inflammatory dermatitis such as psoriasis and chronic urticaria, Guillain-Barre syndrome, and hemolytic uremic syndrome.

Uncontrolled complement activation can also occur in cancer, in pregnancy complications such as preeclamsia and antiphospholipid syndrome, and under acute pathological conditions including sepsis, acute lung injury, acute respiratory distress syndrome (ARDS), and ischemia-reperfusion injury. Massive complement activation is also found on artificial surfaces leading to hemodialysis-associated thrombosis.

Many of the toxic effects seen in these conditions are attributable to the excessive production of the anaphylatoxin C5a which promotes and perpetuates inflammatory reactions. The main function of C5a is chemotaxis and activation of granulocytes, mast cells, and macrophages mediating the release of soluble immune factors. Inhibition or modulation of complement activity has therefore been recognized as a promising therapeutic strategy for many years.

Most complement proteins exist in the plasma as inactive precursors that cleave and activate each other in a proteolytic cascade in response to three different mechanisms: the classical pathway, the lectin-induced, and the alternative pathway. The final result of all three activation cascades is massive amplification of the response and formation of the anaphylatoxins C3a and C5a and the cell-killing membrane attack complex (MAC), a pore causing lysis of cells.

The complement component C5 is a 190 kDa protein and comprises two chains ($\alpha$115 kDa and $\beta$75 kDa). Activation of either complement pathway can generate a C5 convertase enzyme capable of cleaving C5 to C5b and the potent anaphylatoxin C5a. Upon cleavage of C5 a C-terminal neoepitope on the C5a fragment is exposed.

Human C5a is a 74-amino acid long glycoprotein with the molecular weight of 12-14.5 kDa. The molecule is composed of four $\alpha$-helices which are stabilized by three internal disulfid bridges. An asparagine is located at position 64 which has an N-linked carbohydrate moiety that is not essential for biological activity but very likely regulates C5a activity in vivo. Shortly after the cleavage of the C5a fragment by the C5 convertase, the very C-terminal arginine residue of the 74-amino acid long C5a protein is removed by serum and cell surface carboxy-peptidases and the less active C5a desARG molecule is formed. Both forms of the C5a protein, C5a ARG and C5a desARG, bind to the seven-transmembrane domain receptors C5aR (CD88) and the less characterized C5L2 (gpr77), which are ubiquitously expressed on a wide variety of cells but particularly on the surface of immune cells like macrophages, neutrophils, mast cells, and T-cells. The ligand-binding site of C5aR is complex and consists of at least two physically separable binding domains. One binds the C5a disulfide-linked core (amino acids 15-46), while the second binds the C5a carboxy-terminal end (amino acid 67-74). The binding affinity of C5aR to its ligand C5a is very high with a dissociation constant ($K_D$) of about 1 nM.

It is an object of the present invention to provide means and methods for the treatment of complement component C5a induced diseases or pathologies.

The present invention relates to a vaccine comprising at least one peptide consisting of 7 to 19, preferably 7 to 14, amino acid residues consisting of the amino acid sequence $$(X_3)_m KDX_2 QLGX_1, \quad \text{(SEQ ID No. 99)}$$

wherein $X_1$ is an amino acid residue selected from the group consisting of alanine, asparagine, glutamine, glycine, histidine, isoleucine, leucine, lysine, methionine, serine, threonine, tyrosine and valine, $X_2$ is an amino acid residue selected from the group consisting of alanine, arginine, histidine, isoleucine, leucine, lysine, methionine, threonine, tyrosine and valine, $X_3$ is $(X_4)_n ANISX_5$ (SEQ ID No. 100) or an N-terminal truncated fragment thereof consisting of 1 to 4, preferably 1, 2, 3 or 4, amino acid residues, $X_4$ is VVASQLR (SEQ ID No. 101) or an N-terminal truncated fragment thereof consisting of 1 to 6, preferably 1, 2, 3, 4, 5 or 6 amino acid residues, $X_5$ is an amino acid residue selected from the group consisting of alanine, asparagine, glutamine, glutamic acid, histidine, arginine, isoleucine, lysine, methionine, serine and threonine, m is 0 or 1, and n is 0 or 1, wherein said at least one peptide is coupled or fused to a carrier comprising at least one T-cell epitope.

The present invention relates to an active immunization against the body's own C5a, which is up-regulated in various chronic inflammatory diseases. The neo-epitope on the C-terminus of C5a which becomes accessible upon cleavage of the C5 molecule is the immunization target of the present invention. Thus, the generation and function of the C5b fragment, which plays a major role in host defence, will not be affected.

In more detail, the present invention refers to a vaccine based on peptide variants (so called VARIOTOPES) of the original hC5a C-terminal epitope coupled or fused to a carrier comprising at least one T-cell epitope, wherein the VARIOTOPES comprise at least 1 amino acid residue exchange of the original C-terminal sequences of hC5a.

VARIOTOPES mimic epitopes of interest without being identical thereto, thus the advantage of VARIOTOPE vaccines is to elude the autotolerance to self-antigens. Moreover, the use of VARIOTOPES alleviates the risk of unmeant side effects which are prevalent by the use of self-antigens.

VARIOTOPES of the hC5a C-terminal epitope can be identified and selected using, for instance, the "alanine scanning" method. Alanine-scanning mutagenesis refers to a systematic substitution of individual amino acids within a certain protein or peptide region by an alanine residue in order to determine the functional role of certain positions. Alanine is the substitution residue of choice because it eliminates the side chain on the β carbon and does not alter the main chain conformation nor does it impose extreme electrostatic or steric effects.

Using this technology, amino acid residues of the hC5a C-terminal epitope that are either crucial or dispensable for the induction of a humoral immune response to hC5a can be identified. In a next step, the positions which turned out to be exchangeable without impairing the induction of a humoral immune response to hC5a can be systematically substituted by amino acid residues with different characteristics in order to determine VARIOTOPES which are able to induce antibodies with higher or at least equal inhibitory activity against human C5a when compared to the original epitope. Subsequently, combinations of two or three amino acid exchanges within the C-terminal epitope of hC5a can be tested for their immunogenicity and functional activity. VARIOTOPES which are able to induce antibodies which show higher or at least equal inhibitory activity against human C5a compared to the original C-terminal epitope are the object of the present invention.

It surprisingly turned out that a peptide requires the presence of at least the lysine, aspartic acid, glutamine, leucine and glycine residues of SEQ ID No. 99 at positions 2, 3, 5, 6 and 7, respectively, to be able to provoke a satisfactory immune response (FIGS. 1A and 1B). Even more surprisingly is the fact that peptides with an amino acid exchange on the last position ($X_1$ of SEQ ID NO. 99; $X_1$ is an arginine residue in the wild-type C5a C-terminal region, see SEQ ID Nos. 1 to 4) are able to induce a humoral immune response against the C5a protein that was significantly higher than the immune response induced by fragments of the wild-type C5a comprising SEQ ID No. 1 to 4 (FIG. 1A to 1D). Importantly, as depicted in FIG. 2A to 2D the higher humoral immune response resulted also in a significantly higher inhibition of the C5a activity. Similar results can also be observed when peptides that contain an amino acid exchange of the M residue at the $5^{th}$ last position of the wild-type C5a C-terminal region (see e.g. SEQ ID No. 10 or 18) or peptides that contain an amino acid exchange of the H residue at the $8^{th}$ last position of the wild-type C5a C-terminal epitope (see e.g. SEQ ID No. 7 or 17) are used for immunization (FIG. 1 and FIG. 2). This surprising effect that peptides resulting from an amino acid exchange of the abovementioned amino acids (R, M or H at the last, the $5^{th}$ last and the $8^{th}$ last position of the wild-type C5a terminal epitope, respectively; see SEQ ID Nos. 1 to 4, e.g.) have the capacity to induce an C5a specific antibody immune response which is higher and more potent than the immune response induced by fragments of the wild-type C5a comprising SEQ ID No. 1 to 4 is supported by results shown in FIG. 3 to FIG. 6. Here peptides are depicted that show a much higher C5a inhibitory capacity compared to the corresponding wild type C5a fragment.

Irrelevant for the present invention in the WO 90/09162 several peptides are disclosed which show some homologies to human wild type C5a fragments and which are used as agonists of the C5a activity. However, the peptides disclosed therein were applied as soluble peptides that have not been coupled to a carrier protein and thus cannot be used for the purpose of the present invention since they are not able to induce the formation of antibodies inhibiting the C5a activity. In example 426 of the WO 90/09162, for instance, a peptide is disclosed which comprises at position 1 a phenylalanine residue. In the present invention it could be shown that such a substitution results in significantly reduced C5a inhibitory acitivity (see e.g. SEQ ID No. 54, FIG. 4).

The at least one peptide comprised in the vaccine of the present invention comprises or consists of 7, preferably 8, preferably 9, preferably 10, preferably 11, preferably 12, preferably 13, preferably 14, preferably 15, preferably 16, preferably 17, preferably 18, preferably 19 amino acid residues.

According to the present invention $X_3$ is $(X_4)_n$ANIS$X_5$ (SEQ ID No. 100) or an N-terminal truncated fragment thereof. Consequently this N-terminal truncated fragment may consist of ANIS$X_5$ (SEQ ID No. 102), NIS$X_5$ (SEQ ID No. 103), IS$X_5$, S$X_5$ or $X_5$. This means that the vaccine of the present invention may comprise at least one peptide having the amino acid sequence ANIS$X_5$KD$X_2$QLG$X_1$ (SEQ ID No. 104), NIS$X_5$KD$X_2$QLG$X_1$ (SEQ ID No. 105), IS$X_5$KD$X_2$QLG$X_1$ (SEQ ID No. 106), S$X_5$KD$X_2$QLG$X_1$ (SEQ ID No. 107) or $X_5$KD$X_2$QLG$X_1$ (SEQ ID No. 108), if m=1.

According to the present invention $X_4$ is VVASQLR (SEQ ID No. 101) or an N-terminal truncated fragment thereof. The fragment of VVASQLR may consist of one of the following amino acid sequences: VASQLR (SEQ ID No. 109), ASQLR (SEQ ID No. 110), SQLR (SEQ ID No. 111), QLR, LR, or R. Consequently the at least one peptide used in the vaccine of the present invention may have one of the following amino acid sequences: VVASQLRANIS$X_5$KD$X_2$QLG$X_1$ (SEQ ID No. 112), VASQLRANIS$X_5$KD$X_2$QLG$X_1$ (SEQ ID No. 113), ASQLRANIS$X_5$KD$X_2$QLG$X_1$ (SEQ ID No. 114), SQLRANIS$X_5$KD$X_2$QLG$X_1$ (SEQ ID No. 115), QLRANIS$X_5$KD$X_2$QLG$X_1$ (SEQ ID No. 116), LRANIS$X_5$KD$X_2$QLG$X_1$ (SEQ ID No. 117), or RANIS$X_5$KD$X_2$QLG$X_1$ (SEQ ID No. 118), if m and n are 1.

The vaccine of the present invention may comprise more than one peptide according to SEQ ID No. 99. It is particularly preferred that the vaccine comprises at least one peptide having amino acid sequence SEQ ID No. 99. However, the vaccine of the present invention may also comprise at least 2, at least 3, at least 4, or even at least 5 peptides having amino acid sequence SEQ ID No. 99. Of course it is also possible to combine the at least one peptide of the present invention with other peptides or active ingredients which can be used to treat the same conditions as those of the present invention.

The peptide/carrier combination is important since peptides of the present invention do not have the capacity to induce relevant amounts of antibodies when injected without coupling to a carrier. Furthermore, the carrier facilitates the induction of a long lasting antibody response. Thus, the present invention of an active immunization against hC5a offers advantages over employing monoclonal antibodies therapy for treating C5a-based diseases. Shortcomings of monoclonal C5a antibody therapy including the need for repeated infusions of large amounts of antibodies, frequent hospital visits of the patients, and high production costs of humanized antibodies can therefore be circumvented.

The at least one peptide of the present invention can be synthetically produced by chemical synthesis methods which are well known in the art, either as an isolated peptide or as a part of another peptide or polypeptide. Alternatively, at least one peptide can be produced in a microorganism such as bacteria, yeast or fungi, in eukaryote cells such as a mammalian or an insect cell, or in a recombinant virus vector such as adenovirus, poxvirus, herpesvirus, Simliki forest virus, baculovirus, bacteriophage, sindbis virus or sendai virus which produces the compound/peptide which is then isolated and, if desired, further purified. Suitable bacteria for producing the compound/peptide include *E. coli, B. subtilis* or any other bacterium that is capable of expressing peptides. Suitable yeast types for expressing said compound/peptide include *Saccharomyces cerevisiae, Schizosaccharomyces pombe, Candida* spp., *Pichia pastoris* or any other yeast capable of expressing peptides. Corresponding methods are well known in the art. Methods for isolating and purifying recombinantly produced peptides are also well known in the art and include e.g. a gel filtration, affinity chromatography, ion exchange chromatography etc.

To facilitate isolation of the compound/peptide, a fusion polypeptide may be generated wherein the compound/peptide is translationally fused (covalently linked) to a heterologous polypeptide which enables isolation by affinity chromatography. Typical heterologous polypeptides are His-Tag (e.g. His6; 6 histidine residues), GST-Tag (Glutathione-S-transferase) etc. The fusion polypeptide facilitates not only the purification of the compound/peptide but may also prevent the degradation of said compound/peptide during purification. If it is desired to remove the heterologous polypeptide after purification, the fusion polypeptide may comprise a cleavage site at the junction between the compound/peptide and the heterologous polypeptide. The cleavage site consists of an amino acid sequence that is cleaved with an enzyme specific for the amino acid sequence at the site (e.g. proteases).

$X_1$ can be a nonpolar, alipathic amino acid residue such as A, G, V, L, M or I; a polar, uncharged amino acid residue such as S, T, N or Q; a positively charged amino acid residue such as K or H; or a polar aromatic amino acid residue such as Y. $X_2$ can be an amino acid residue selected from the group of A, M, V, L, I, K, R, H, T and Y. $X_5$ can be a nonpolar, alipathic amino acid residue such as A, M, I; a polar, uncharged amino acid residue such as S, T, N or Q; or a charged amino acid residue such as K, R, H or E.

According to a preferred embodiment of the present invention $X_1$ is an amino acid residue selected from the group consisting of threonine, glutamine, tyronsine, methionine, alanine, glycine, and valin.

A further preferred embodiment of the present invention $X_1$ is an amino acid residue selected from the group consisting of alanine, asparagine, glutamine, histidine, lysine, methionine, serine, and threonine if m is 1 and $X_5$ is an amino acid residue selected from the group consisting of alanine, histidine, methionine and threonine, and/or $X_2$ is an amino acid residue selected from the group consisting of methionine, alanine, lysine and valine.

According to a particularly preferred embodiment of the present invention m is 1 and $X_5$ is an amino acid residue selected from the group consisting of alanine, methionine and threonine.

According to a preferred embodiment of the present invention $X_2$ is an amino acid residue selected from the group consisting of methionine, alanine, lysine and valine.

According to a further preferred embodiment of the present invention the at least one peptide is selected from the group consisting of ISHKDMQLGA (SEQ ID No. 14), ANISHKDMQLGA (SEQ ID No. 21), KDMQLGA (SEQ ID No. 22), VVASQLRANISHKDMQLGA (SEQ ID No. 23), ANISHKDMQLGT (SEQ ID No. 24), ANISHKDMQLGQ (SEQ ID No. 25), ANISHKDMQLGY (SEQ ID No. 26), ANISHKDMQLGM (SEQ ID No. 27), ANISHKDMQLGG (SEQ ID No. 28), ANISHKDMQLGV (SEQ ID No. 29), ANISHKDMQLGK (SEQ ID No. 30), ANISHKDMQLGS (SEQ ID No. 31), ANISHKDMQLGH (SEQ ID No. 32), ANISHKDMQLGN (SEQ ID No. 33), ANISHKDMQLGL (SEQ ID No. 34), ANISHKDMQLGA (SEQ ID No.70), ANISHKDMQLGQ (SEQ ID No. 71), ANISHKDMQLGS (SEQ ID No. 72), ANISHKDMQLGM (SEQ ID No. 73), ANISMKDMQLGN (SEQ ID No. 74), ANISTKDKQLGM (SEQ ID No. 75), ANISMKDMQLGH (SEQ ID No. 76), ANISAKDMQLGA (SEQ ID No. 77), ANISMKDMQLGA (SEQ ID No. 78), ANISTKDKQLGA (SEQ ID No. 79), ANISAKDAQLGA (SEQ ID No. 80), ANISMKDMQLGS (SEQ ID No. 81), ANISHKDMQLGA (SEQ ID No. 82), ANISHKDMQLGN (SEQ ID No. 83), ANISTKDMQLGK (SEQ ID No. 84), ANISMKDMQLGM (SEQ ID No. 85), ANISTKDMQLGT (SEQ ID No. 86), ANISHKDKQLGK (SEQ ID No. 87), ANISMKDMQLGH (SEQ ID No. 88), and ANISAKDAQLGA (SEQ ID No. 89).

According to a particularly preferred embodiment at least one peptide consisting of amino acid sequence SEQ ID No. 99 comprises at its N- and/or C-terminus at least one cysteine residue bound directly or via a spacer sequence thereto.

This cysteine residue may serve as a reactive group in order to bind the peptide to another molecule or a carrier. For instance, this group may be used to bind the peptide to a carrier protein. The cysteine residue can be bound directly to the peptides of the present invention or via a spacer sequence. The spacer sequence comprises preferably at least one, preferably at least two, more preferably at least three, even more preferably at least four, and optionally a maximum of ten, preferably a minimum of five small non-polar amino acid residues such as glycines.

According to a preferred embodiment of the present invention the carrier is selected from the group consisting of keyhole limpet haemocyanin (KLH), CRM197, tetanus toxoid (TT), diphtheria toxin (DT), protein D or any other protein or peptide containing T-cell epitopes.

According to the present invention the peptide is coupled or fused to a pharmaceutically acceptable carrier, preferably KLH (Keyhole Limpet Haemocyanin), tetanus toxoid, albumin-binding protein, bovine serum albumin, a dendrimer, peptide linkers (or flanking regions) as well as the adjuvant substances described in Singh et al. (Singh et al., Nat. Biotech. 17, (1999): 1075-1081 (in particular those in Table 1 of that document)), and O'Hagan et al. (O'Hagan and Valiante, Nature Reviews, Drug Discovery 2 (9); (2003): 727-735 (in particular the endogenous immuno-potentiating compounds and delivery systems described therein)), or mixtures thereof. The conjugation chemistry (e.g. via hetero-bifunctional compounds such as GMBS and of course also others as described in "Bioconjugate Techniques", Greg T. Hermanson) in this context can be selected from reactions known to the skilled man in the art.

Alternatively it is also possible to fuse the at least one peptide of the present invention to a protein carrier by methods known in the art. Such proteins comprise a peptide as described herein together with an unrelated immunogenic protein. Preferably the immunogenic protein is capable of eliciting a recall response. Examples of such proteins include tetanus, tuberculosis, hepatitis proteins and protein D, a surface protein of the gram-negative bacterium *Haemophilus influenza* B (WO 91/18926). Preferably a protein D derivative is used which comprises approximately the first third of the protein (e.g., the first N-terminal 100-110 amino acids) and which may be lipidated. Another carrier which may be used to provide fusion proteins may be the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; Gene 43; (1986):265-292). LYTA is an autolysin that specifically degrades certain bonds in the peptidoglycan backbone. Within a preferred embodiment, a repeat portion of LYTA may be incorporated into a fusion protein. A repeat portion is found in the C-terminal region starting at residue 178. A particularly preferred repeat portion incorporates residues 188-305.

According to a preferred embodiment of the present invention the peptide is formulated with an adjuvant, preferably adsorbed to alum.

The vaccine according to the present invention may be formulated with an adjuvant, preferably a low soluble aluminum composition, in particular aluminum hydroxide. Of course, also adjuvants like MF59, aluminum phosphate, calcium phosphate, cytokines (e.g. IL-2, IL-12, GM-CSF), saponins (e.g. QS21), MDP derivatives, CpG oligos, LPS, MPL, polyphosphazenes, emulsions (e.g. Freund's, SAF), liposomes, virosomes, iscoms, cochleates, PLG microparticles, poloxamer particles, virus-like particles, heat-labile enterotoxin (LT), cholera toxin (CT), mutant toxins (e.g. LTK63 and LTR72), microparticles and/or polymerized liposomes may be used.

Suitable adjuvants are commercially available as, for example, AS01B, AS02A, AS15, AS-2 and derivatives thereof (GlaxoSmithKline, Philadelphia, Pa.); CWS, TDM, Leif, aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF or interleukin-2, -7 or -12 may also be used as adjuvants.

Within the vaccines provided herein, the adjuvant composition is preferably designed to induce an immune response predominantly of the Th1 type. High levels of Th1-type cytokines (e.g., IFN-y, TNFct, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses.

Following application of a vaccine as provided herein, a patient will support an immune response that includes Th1 and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines see Janeway et al., Immunobiology, 5$^{th}$ Edition, 2001.

Preferred adjuvants for use in eliciting a predominantly Th1-type response include, for example, a combination of monophosphoryl lipid A, preferably 3-O-deacylated monophosphoryl lipid A (3D-MPL), optionally with an aluminum salt (see, for example, Ribi et al., Immunology and Immunopharmacology of Bacterial Endotoxins, Plenum Publ. Corp., NY, (1986): 407-419; GB 2122204B; GB 2220211; and U.S. Pat. No. 4,912,094). A preferred form of 3D-MPL is an emulsion having a small particle size less than 0.2 mm in diameter, and its method of manufacture is disclosed in WO 94/21292. Aqueous formulations comprising monophosphoryl lipid A and a surfactant have been described in WO 98/43670. Exemplified preferred adjuvants include AS01B (MPL and QS21 in a liposome formulation), 3D-MPL and QS21 in a liposome formulation, AS02A (MPL and QS21 and an oil-in-water emulsion), 3D-MPL and QS21 and an oil-in-water emulsion, and AS 15, available from GlaxoSmithKline. MPL adjuvants are available from GlaxoSmithKline, Seattle, Wash. (see U.S. Pat. Nos. 4,436,727; 4,877,611; 4,866,034 and 4,912,094).

CpG-containing oligonucleotides (in which the CpG dinucleotide is unmethylated) also induce a predominantly Th1 response. CpG is an abbreviation for cytosine-guanosine dinucleotide motifs present in DNA. Such oligonucleotides are well known and are described, for example, in WO 96/02555, WO 99/33488, U.S. Pat. Nos. 6,008,200 and 5,856,462. Immunostimulatory DNA sequences are also described, for example, by Sato et al., Science 273; (1996): 352. CpG when formulated into vaccines is generally administered in free solution together with free antigen (WO 96/02555; McCluskie and Davis, supra) or covalently conjugated to an antigen (WO 98/16247), or formulated with a carrier such as aluminium hydroxide ((Hepatitis surface antigen) Davis et al., supra; Brazolot-Millan et al., PNAS USA, 95(26), (1998):15553-8). CpG is known in the art as being an adjuvant that can be administered by both systemic and mucosal routes (WO 96/02555, EP 0 468 520, Davis et al., J. Immunol, 160(2), (1998):870-876; McCluskie and Davis, J. Immunol., 161(9), (1998):4463-6).

Another preferred adjuvant is a saponin or saponin mimetics or derivatives, preferably QS21 (Aquila Biopharmaceuticals Inc.), which may be used alone or in combination with other adjuvants. For example, an enhanced system involves the combination of a monophosphoryl lipid A and saponin derivative, such as the combination of QS21 and 3D-MPL as described in WO 94/00153, or a less reactogenic composition where the QS21 is quenched with cholesterol as described in WO 96/33739. Other preferred formulations comprise an oil-in-water emulsion and tocopherol. A particularly potent adjuvant formulation involving QS21, 3D-MPL and tocopherol in an oil-in-water emulsion is described in WO 95/17210. Additional saponin adjuvants of use in the present invention include QS7 (described in WO 96/33739 and WO 96/11711) and QS17 (described in U.S. Pat. No. 5,057,540 and EP 0 362 279 B1).

Other preferred adjuvants include Montanide ISA 720 (Seppic, France), SAF (Chiron, Calif., United States), ISCOMS (CSL), MF-59 (Chiron), the SBAS series of adjuvants (e.g., SBAS-2, AS2', AS2, SBAS-4, or SBAS6, available from GlaxoSmithKline), Detox (Corixa), RC-529 (Corixa, Hamilton, Mont.) and other aminoalkyl glucosaminide 4-phosphates (AGPs). Further example adjuvants include synthetic MPL and adjuvants based on Shiga toxin B subunit (see WO 2005/112991).

The vaccine of the present invention may be administered subcutaneously, intramuscularly, intradermally, intravenously (see e.g. "Handbook of Pharmaceutical Manufacturing Formulations", Sarfaraz Niazi, CRC Press Inc, 2004). Depending on the route of administration, the medicament may comprise respective carriers, adjuvants, and/or excipients.

The vaccine according to the present invention contains the compound according to the invention in an amount of 0.1 ng to 10 mg, preferably 10 ng to 1 mg, in particular 100 ng to 100 µg, or, alternatively, e.g. 100 fmol to 10 µmol, preferably 10 pmol to 1 µmol, in particular 100 pmol to 100 nmol. The compound or peptide of the present invention is administered to a mammal in an amount of preferably 100 ng to 1 mg, more preferably 1 µg to 500 µg, even more preferably 10 µg to 100 µg, in particular 20 to 40 or 30 µg, per doses. Typically, the vaccine may also contain auxiliary substances, e.g. buffers, stabilizers etc. The vaccine according to the present invention is applied 3 to 6 times in a time interval of two weeks up to 2 month. Upon existing of anti C5a antibodies the vaccine is applied in regular intervals of approximately 6 months.

According to a preferred embodiment of the present invention the vaccine is used in the treatment of a complement-mediated disorder (see e.g. Allegretti M et al, Curr Med Chem 12(2005):217-236). Thus the present invention relates also to a method for treating an individual suffering from a complement-mediated disorder by administering a vaccine according to the present invention.

The complement-mediated disorder is preferably an inflammatory disease, preferably a chronic inflammatory disease.

The inflammatory disease is preferably selected from the group consisting of age-related macular degeneration (AMD), a neurodegenerative disorder, preferably Alzheimer's disease, Parkinson's disease or Huntington's disease, allergic asthma, atherosclerosis, Guillain-Barre syndrome, vasculitis, inflammatory dermatitis, preferably psoriasis and urticaria, rheumatoid arthritis, antiphospholipid syndrome (APS), multiple sclerosis, hemolytic uremic syndrome, and systemic lupus erythematosus (SLE).

The complement-mediated disorder is preferably ischemia-reperfusion injury, acute lung injury, acute respiratory distress syndrome (ARDS), sepsis, cancer, pregnancy complications such as preeclampsia, recurrent spontaneous abortions, intrauterine growth retardation and APS.

A complement-mediated disorder—according to the present invention—is also a disorder which involves undesirable or inappropriate complement activity such as hemodialysis-associated thrombosis. This activity can be determined by methods known in the art. The disorders which can be treated with the vaccine according to the present invention are characterized by an increased C5a activity.

AMD is a medical condition which usually affects older adults and results in a loss of vision in the center of the visual field (the macula) because of damage to the retina. It occurs in "dry" and "wet" forms, whereas the dry form accounts for 90% of all AMD instances. One of the earliest clinical hallmarks of wet and dry AMD is the appearance of amorphous lipoproteinaceous deposits accumulating extra-cellularly in areas close to the retinal pigment epithelium. These pathogenic components are called drusen. Recent studies have implicated local inflammation and activation of the complement cascade in the formation of drusen, the hallmark of dry AMD. This is in line with other studies showing that beside other molecules the complement component C5, accumulates within these drusen.

Moreover, it has been shown that C5a, besides VEGF (C5a is involved in the release of VEGF), plays a key role in the induction of the choroidal neovascularization, which takes place in the wet form of AMD. Most importantly, the neutralizing antibodies against C5a could be shown to be able to stop the progression of the disease in animal models.

Taken together, there is strong support for complement-mediated disease in wet and dry forms of AMD and thus C5a appears to be an optimal target for the treatment of both forms of AMD Complement-mediated inflammation, predominately caused by C5a, is proposed to play a role in the acceleration or progression of Alzheimer's disease. Prolonged complement activation is triggered by fibrillar Aβ plaques in Alzheimer's disease brain and many manifestations of the disease can be contributed to C5a-recruited and activated glia that promote inflammatory events. Similar events may apply to Parkinson's disease and Huntington's disease. Furthermore, preliminary data indicate a specific pathogenic role for the activation fragment of complement C5 (C5a) in motor neuron disease, a group of degenerative disorders causing progressive motor neuron death leading to eventual paralysis and death.

Blockage of C5aR clearly reduces airway inflammation and airway hyper-responsiveness in experimental allergic asthma. However, the role of complement component C5 in asthma remains controversial. C5 has been described as either promoting or protecting against airway hyper-responsiveness in experimental allergic asthma, suggesting a dual role for C5a in allergic asthma. One hypothesis is that C5aR signaling during allergen sensitization protects from the development of pulmonary allergy but enhances the allergic phenotype in an inflamed pulmonary environment during the effector phase. Thus, C5aR blockage might be of therapeutic benefit for the treatment of established asthma.

C5a plays also a role in atherosclerosis. C3a and C5a are expressed in human coronary plaques. Moreover, it has recently been shown that C5a predicts cardiovascular events in patients with advanced atherosclerosis and that elevated serum levels of C5a are associated with the development of restenosis after balloon angioplasty of the superficial femoral artery.

Vasculitis is an inflammatory process of blood vessels, histopathologically characterized by inflammation and fibrinoid necrosis of the vessel wall. The clinical spectrum of this form of vasculitis is variable ranging from purpura to severe proliferative glomerulonephritis and the complement systems is supposed to be critically involved in these processes. For instance, C5a plays an important role in anti-neutrophil cytoplasmic autoantibody (ANCA)-associated vasculitis, a relatively uncommon but potentially life-threatening systemic autoimmune disease. ANCA-induced necrotizing crescentic glomerulonephritis requires complement participation in its pathogenesis. C5a and the neutrophil C5aR may compose an amplification loop for ANCA-mediated neutrophil activation. The C5aR may provide a new therapeutic target for ANCA-induced necrotizing crescentic glomerulonephritis.

Complement activation is involved in the pathogenesis of the inflammatory changes in autoimmune dermatitis including bullous pemphigoid (BP), psoriasis vulgaris, and chronic urticaria. In pemphigus complement activation by pemphigus antibody in the epidermis seems to be responsible for the development of characteristic inflammatory changes termed eosinophilic spongiosis. In psoriatic scales high levels of C5a are found, indicating that complement activation is involved in this disease. Psoriasis is known to be a T-cell mediated disease, however, neutrophils and mast cells may also be involved in the pathogenesis of the disease. T-cells and neutrophils are chemo-attracted by C5a, therefore C5a could be an important therapeutic target for treatment of psoriasis.

Complement activation also contributes to the autoimmune inflammatory disease, rheumatoid arthritis. It appears that anaphylatoxin C5a is the main product of complement activation responsible for tissue damage in rheumatoid arthritis although deposition of membrane attack complex as well as opsonization with fragments of C3b are also important.

The role of complement in the pathogenesis of systemic lupus erythematosus (SLE) remains controversial. On the one hand, complement components appear to mediate autoantibody-initiated tissue damage. On the other hand, the complement system appears to have protective features as hereditary deficiencies of some complements are associated with an increased risk for SLE. It is known that patients with SLE often have hypocomplementemia. Moreover, it was demonstrated that C5a/C5aR signaling plays an important role in the pathogenesis of central nervous system lupus by regulating the integrity of the blood-brain barrier. The potential of C5a/C5aR blockage was highlighted as a promising therapeutic strategy in SLE.

It appears that the tissue reperfusion (R) and not the ischemia (I) activates complement and leads to inflammation-induced damage. Even though exact involvement of complement activation in I/R injury is still unclear, several experimental studies have indicated a connection between complement and the pathogenesis of I/R injury, and have suggested complement inhibition as a potent therapy. For instance, in a murine myocardial I/R injury model a systemic C5 inhibition, 30 minutes prior to reperfusion, significantly protected mice from myocardial I/R injury.

Complement activation has been demonstrated in many forms of acute lung injury. C5a concentration is increased in bronchoalveolar lavage fluids (BALF) in acute lung injury induced by acid instillation, and C5a concentration is also elevated in transplanted lungs in human. C5a attracts neutrophils into the lung and directly actives neutrophils, macrophages, and endothelial cells. The protective role of anti-C5a was associated with drastic reduction in BALF levels of TNF-α, as well as a profound decrease in lung vascular intercellular adhesion molecule ICAM-1 expression, suggesting that C5a is essential in the foundation of the inflammatory network, regulating the expression of inflammatory mediators and expression of adhesion molecules.

Acute lung injury and acute respiratory distress syndrome (ARDS) is characterized by the presence of fibrin-rich inflammatory exudates in the intra-alveolar spaces and the extensive migration of neutrophils into alveoli of the lungs. Pharmacological blockade of TNF-α and C5a signaling in neutrophils from healthy volunteers was able to significantly diminish the BALF induced procoagulant activity of these otherwise normal cells and cause a concomitant loss of tissue factor (TF) expression. These results indicate that C5a and TNF-α signaling contributes to the induction of TF expression in neutrophils accumulating in the alveoli of lungs affected by ARDS.

During the onset of sepsis, the inflammatory system becomes hyperactive, involving both cellular and humoral defense mechanism. It has been shown that complement activation during human sepsis, especially as reflected in elevated levels of C5a, is associated with significantly reduced survival rates together with multi-organ failure when compared with less severe septic patients and survivors. Moreover, interception of either C5a or C5aR dramatically improves survival during experimental sepsis in rodents. Thus, C5a seems to be a key player for the development of sepsis and interference of C5a/C5aR binding may present a potent clinical approach for preventive treatment of patients at high risk for developing sepsis.

In cardiopulmonary bypass and hemodialysis, C5a is generated as a result of activation of the alternative complement pathway when human blood makes contact with the artificial surface of the heart-lung machine or kidney dialysis machine. C5a causes increased capillary permeability and edema, bronchoconstriction, pulmonary vasoconstriction, leukocyte and platelet activation and infiltration to tissues, in particular the lung. Administration of an anti-C5a monoclonal antibody was shown to reduce cardiopulmonary bypass and cardioplegia-induced coronary endothelial dysfunction.

Tumor-driven complement activation can provide tumor growth advantage. The generation of complement C5a in a tumor microenvironment enhances tumor growth by suppressing the antitumor $CD8^+$ T-cell mediated response. Using a mouse model of tumor growth revealed that deficiency or blockage of C5aR is associated with retardation of tumor growth. Complement inhibition is therefore considered as an effective and promising approach in anticancer therapy.

A significant increase of complement activation was associated with different pathologic pregnancy outcomes, namely preeclampsia, recurrent spontaneous abortions, intra-uterine growth retardation, and antiphospholipid syndrome (APS). Women with preeclampsia showed increased plasma concentration of C5a compared to normal pregnant women. Concerning APS, antiphospholipid antibodies and complement activation (via C3a, C5a, and MAC) may cooperate in triggering a local inflammatory process, eventually leading to placental thrombosis, hypoxia, and neutrophil infiltration. Tissue factor (TF) represents the link between C5a and neutrophil activation in antiphospholipid antibody induced fetal injury.

Summarizing, the peptide-induced immune response against C5a results in an effective therapy for C5a mediated (chronic inflammatory) diseases including neurodegenerative diseases such as Alzheimer's disease (see e.g. Fonseca, M. I. et al. (2009), J Immunol "Treatment with a C5aR Antagonist Decreases Pathology and Enhances Behavioral Performance in Murine Models of Alzheimer's Disease." and Klos, A. et al. (2009), Mol Immunol "The role of the anaphylatoxins in health and disease."), Parkinson's disease (see e.g. McGeer, P. L. et al. (2004), Parkinsonism Relat Disord "Inflammation and neurodegeneration in Parkinson's disease."), Huntington's disease (see e.g. Singhrao, S. K. et al. (1999), Exp Neurol "Increased complement biosynthesis by microglia and complement activation on neurons in Huntington's disease.") and age-related macula degeneration (see e.g. Nozaki, M. et al. (2006), Proc Natl Acad Sci "Drusen complement components C3a and C5a promote choroidal neovascularization."), rheumatoid arthritis (see e.g. Okroj, M. et al. (2007), Ann Med "Rheumatoid arthritis and the complement system."), systemic lupus erythematosus (SLE) (see e.g. Chen, M. et al. (2009), J Autoimmun "The complement system in systemic autoimmune disease."; Jacob, A. et al. (2010), J Neuroimmunol "Inhibition of C5a receptor alleviates experimental CNS lupus." and Jacob, A, et al. (2010), FASEB J "C5a alters blood-brain barrier integrity in experimental lupus."), asthma (see e.g. Kohl, J. et al. (2006), J Clin Invest "A regulatory role for the C5a anaphylatoxin in type 2 immunity in asthma."), vasculitis, antiphospholipid syndrome (APS), atherosclerosis, inflammatory dermatitis such as psoriasis and chronic urticaria, Guillain-Barre syndrome, hemolytic uremic syndrome, and multiple sclerosis. Since uncontrolled hC5a release contributes to other pathological conditions such as ischemia and reperfusion injury, sepsis, acute lung injury, complications associated with hemodialysis, cancer, pregnancy complication such as preeclamsia and APS, neutralization of C5a by active immunization may provide an effective therapy for these pathological complications as well.

"Treating", as used herein, refers to providing treatment, i.e, providing any type of medical or surgical management of a subject. The treatment can be provided in order to reverse, alleviate, inhibit the progression of, prevent or reduce the likelihood of a disease, disorder, or condition, or in order to reverse, alleviate, inhibit or prevent the progression of, prevent or reduce the likelihood of one or more symptoms or manifestations of a disease, disorder or condition. "Prevent" refers to causing a disease, disorder, condition, or symptom or manifestation of such not to occur for at least a period of time in at least some individuals. Treating can include administering an agent to the subject following the development of one or more symptoms or manifestations indicative of a complement-mediated condition, e.g., in order to reverse, alleviate, reduce the severity of, and/or inhibit or prevent the progression of the condition and/or to reverse, alleviate, reduce the severity of, and/or inhibit or one or more symptoms or manifestations of the condition. A composition of the present invention can be administered to a subject who has developed a complement-mediated disorder or is at increased risk of developing such a disorder relative to a member of the general population. A composition of this invention can be administered prophylactically, i.e., before development of any symptom or manifestation of the condition. Typically in this case the subject will be at risk of developing the condition.

Another aspect of the present invention relates to a peptide consisting of 7 to 19 amino acid residues consisting of the amino acid sequence $$(X_3)_m KDX_2 QLGX_1,$$ (SEQ ID No. 99)

wherein $X_1$ is an amino acid residue selected from the group consisting of alanine, asparagine, glutamine, glycine, histidine, isoleucine, leucine, lysine, methionine, serine, threonine, tyrosine and valine, $X_2$ is an amino acid residue selected from the group consisting of alanine, arginine, histidine, isoleucine, leucine, lysine, methionine, threonine, tyrosine and valine, $X_3$ is $(X_4)_n ANISX_5$ (SEQ ID No. 100) or an N-terminal truncated fragment thereof consisting of 1 to 4 amino acid residues, $X_4$ is VVASQLR (SEQ ID No. 101) or an N-terminal truncated fragment thereof consisting of 1 to 6 amino acid residues, $X_5$ is an amino acid residue selected from the group consisting of alanine, asparagine, glutamine, glutamic acid, histidine, arginine, isoleucine, lysine, methionine, serine and threonine, m is 0 or 1, and n is 0 or 1, wherein said at least one peptide is coupled or fused to a carrier comprising at least one T-cell epitope.

According to a preferred embodiment of the present invention $X_1$ is an amino acid residue selected from the group consisting of threonine, glutamine, tyronsine, methionine, alanine, glycine, and valine.

$X_1$ is preferably an amino acid residue selected from the group consisting of alanine, asparagine, glutamine, histidine, lysine, methionine, serine, and threonine if m is 1 and $X_5$ is an amino acid residue selected from the group consisting of alanine, histidine, methionine and threonine, preferably alanine, threonine or methionine, and/or $X_2$ is an amino acid residue selected from the group consisting of methionine, alanine, lysine and valine.

According to a particularly preferred embodiment of the present invention m is 1 and $X_5$ is an amino acid residue selected from the group consisting of alanine, histidine, methionine and threonine, preferably alanine, threonine, or methionine.

According to another preferred embodiment of the present invention $X_2$ is an amino acid residue selected from the group consisting of methionine, alanine, lysine and valine.

According to a particularly preferred embodiment of the present invention the peptide is selected from the group consisting of ISHKDMQLGA (SEQ ID No. 14), ANISHKDMQLGA (SEQ ID No. 21), KDMQLGA (SEQ ID No. 22), VVASQLRANISHKDMQLGA (SEQ ID No. 23), ANISHKDMQLGT (SEQ ID No. 24), ANISHKDMQLGQ (SEQ ID No. 25), ANISHKDMQLGY (SEQ ID No. 26), ANISHKDMQLGM (SEQ ID No. 27), ANISHKDMQLGG (SEQ ID No. 28), ANISHKDMQLGV (SEQ ID No. 29), ANISHKDMQLGK (SEQ ID No. 30), ANISHKDMQLGS (SEQ ID No. 31), ANISHKDMQLGH (SEQ ID No. 32), ANISHKDMQLGN (SEQ ID No. 33), ANISHKDMQLGL (SEQ ID No. 34), ANISMKDMQLGA (SEQ ID No. 70), ANISTKDMQLGQ (SEQ ID No. 71), ANISMKDMQLGS (SEQ ID No. 72), ANISMKDMQLGM (SEQ ID No. 73), ANISMKDMQLGN (SEQ ID No. 74), ANISTKDKQLGM (SEQ ID No. 75), ANISMKDMQLGH (SEQ ID No. 76), ANISAKDMQLGA (SEQ ID No. 77), ANISMKDMQLGA (SEQ ID No. 78), ANISTKDKQLGA (SEQ ID No. 79), ANISAKDAQLGA (SEQ ID No. 80), ANISMKDMQLGS (SEQ ID No. 81), ANISMKDMQLGA (SEQ ID No. 82), ANISHKDMQLGN (SEQ ID No. 83), ANISTKDMQLGK (SEQ ID No. 84), ANISMKDMQLGM (SEQ ID No. 85), ANISTKDMQLGT (SEQ ID No. 86), ANISHKDKQLGK (SEQ ID No. 87), ANISMKDMQLGH (SEQ ID No. 88) and ANISAKDAQLGA (SEQ ID No. 89).

Another aspect of the present invention relates to vaccine comprising at least one peptide consisting of 7 to 19 amino acid residues consisting of the amino acid sequence $$(X_3)_m KDX_2 QLGX_1,$$ (SEQ ID No. 99)

wherein $X_1$ is an amino acid residue selected from the group consisting of arginine, alanine, asparagine, glutamine, glycine, histidine, isoleucine, leucine, lysine, methionine, serine, threonine, tyrosine and valine, most preferably arginine, $X_2$ is an amino acid residue selected from the group consisting of alanine, arginine, histidine, isoleucine, leucine, lysine, threonine, tyrosine and valine, preferably alanine, valine, threonine, tyrosine or leucine, more preferably valine, $X_3$ is $(X_4)_n ANISX_5$ (SEQ ID No. 100) or an N-terminal truncated fragment thereof consisting of 1 to 4 amino acid residues, $X_4$ is VVASQLR (SEQ ID No. 101) or an N-terminal truncated fragment thereof consisting of 1 to 6 amino acid residues, $X_5$ is an amino acid residue selected from the group consisting of alanine, asparagine, glutamine, glutamic acid, histidine, arginine, isoleucine, lysine, methionine, serine and threonine, most preferably histidine, m is 0 or 1, and n is 0 or 1, wherein said at least one peptide is coupled or fused to a carrier comprising at least one T-cell epitope.

Yet, another aspect of the present invention relates to vaccine comprising at least one peptide consisting of 7 to 19 amino acid residues consisting of the amino acid sequence $$(X_3)_m KDX_2 QLGX_1,$$ (SEQ ID No. 99)

wherein $X_1$ is an amino acid residue selected from the group consisting of arginine, alanine, asparagine, glutamine, glycine, histidine, isoleucine, leucine, lysine, methionine, serine, threonine, tyrosine and valine, most preferably arginine, X$_2$ is an amino acid residue selected from the group consisting of alanine, arginine, histidine, isoleucine, leucine, lysine, methionine, threonine, tyrosine and valine, preferably methionine, X$_3$ is (X$_4$)$_n$ANISX$_5$ (SEQ ID No. 100) or an N-terminal truncated fragment thereof consisting of 1 to 4 amino acid residues, X$_4$ is VVASQLR (SEQ ID No. 101) or an N-terminal truncated fragment thereof consisting of 1 to 6 amino acid residues, X$_5$ is an amino acid residue selected from the group consisting of alanine, asparagine, glutamine, glutamic acid, arginine, isoleucine, lysine, methionine, serine and threonine, preferably threonine, glutamine, glutamic acid, serine, lysine or asparagine, more preferably threonine or glutamine, m is 0 or 1, and n is 0 or 1, wherein said at least one peptide is coupled or fused to a carrier comprising at least one T-cell epitope.

According to a preferred embodiment of the present invention X$_3$ is (X$_4$)$_n$ANISX$_5$ (SEQ ID No. 100) or an N-terminal truncated fragment thereof and X$_1$ is arginine. Consequently this N-terminal truncated fragment may consist of ANISX$_5$ (SEQ ID No. 102), NISX$_5$ (SEQ ID No. 103), ISX$_5$, SX$_5$ or X$_5$. This means that the vaccine of the present invention may comprise at least one peptide having the amino acid sequence ANISX$_5$KDX$_2$QLGR (SEQ ID No. 119), NISX$_5$KDX$_2$QLGR (SEQ ID No. 120), ISX$_5$KDX$_2$QLGR (SEQ ID No. 121), SX$_5$KDX$_2$QLGR (SEQ ID No. 122) or X$_5$KDX$_2$QLGR (SEQ ID No. 123), if m=1.

According to a preferred embodiment of the present invention X$_4$ is VVASQLR (SEQ ID No. 101) or an N-terminal truncated fragment thereof. The fragment of VVASQLR may consist of one of the following amino acid sequences: VASQLR (SEQ ID No. 109), ASQLR (SEQ ID No. 110), SQLR (SEQ ID No. 111), QLR, LR, or R. Consequently the at least one peptide used in the vaccine of the present invention may have one of the following amino acid sequences: VVASQLRANISX$_5$KDX$_2$QLGR (SEQ ID No. 124), VASQLRANISX$_5$KDX$_2$QLGR (SEQ ID No. 125), ASQLRANISX$_5$KDX$_2$QLGR (SEQ ID No. 126), SQLRANISX$_5$KDX$_2$QLGR (SEQ ID No. 127), QLRANISX$_5$KDX$_2$QLGR (SEQ ID No. 128), LRANISX$_5$KDX$_2$QLGR (SEQ ID No. 129), or RANISX$_5$KDX$_2$QLGR (SEQ ID No. 130), if m and n are 1.

In a particularly preferred embodiment of the present invention X$_5$ of SEQ ID No. 119 to 130 is histidine if X$_2$ is an amino acid residue as defined above and not methionine.

In a further preferred embodiment of the present invention X$_2$ of SEQ ID No. 119 to 130 is methionine if X$_5$ is an amino acid residue as defined above and not histidine.

According to a particular preferred embodiment of the present invention the peptide is selected from the group consisting of ANISHKDVQLGR (SEQ ID No. 56), ANISHKDTQLGR (SEQ ID No. 57), ANISHKDYQLGR (SEQ ID No. 58), ANISHKDLQLGR (SEQ ID No. 59), ANISHKDAQLGR (SEQ ID No. 18), ANISTKDMQLGR (SEQ ID No. 39), ANISQKDMQLGR (SEQ ID No. 40), ANISEKDMQLGR (SEQ ID No. 41), ANISSKDMQLGR (SEQ ID No. 42), ANISKKDMQLGR (SEQ ID No. 43) and ANISNKDMQLGR (SEQ ID No. 44), preferably selected from the group consisting of ANISHKDVQLGR (SEQ ID No. 56), ANISTKDMQLGR (SEQ ID No. 39) and ANISQKDMQLGR (SEQ ID No. 40).

A further aspect of the present invention relates to a peptide selected from the group consisting of ANISHKDVQLGR (SEQ ID No. 56), ANISHKDTQLGR (SEQ ID No. 57), ANISHKDYQLGR (SEQ ID No. 58), ANISHKDLQLGR (SEQ ID No. 59), ANISHKDAQLGR (SEQ ID No. 18), ANISTKDMQLGR (SEQ ID No. 39), ANISQKDMQLGR (SEQ ID No. 40), ANISEKDMQLGR (SEQ ID No. 41), ANISSKDMQLGR (SEQ ID No. 42), ANISKKDMQLGR (SEQ ID No. 43) and ANISNKDMQLGR (SEQ ID No. 44), preferably selected from the group consisting of ANISHKDVQLGR (SEQ ID No. 56), ANISTKDMQLGR (SEQ ID No. 39) and ANISQKDMQLGR (SEQ ID No. 40).

The present invention is further illustrated by the following figures and examples, however, without being restricted thereto.

FIG. 1 shows an alanine scan (SEQ ID Nos: 5-23) of C-terminal fragments of various length of hC5a (SEQ ID Nos: 1-4) in order to define positions which can be exchanged without abrogating the immunogenicity and the ability to induce antibodies against hC5a. FIG. 1(A) shows the immunogenicity (depicted as titers) of the original epitope hC5a position 65-74 (SEQ ID No: 1) and VARIOTOPES thereof, (B) of the original epitope hC5a position 63-74 (SEQ ID No: 2) and VARIOTOPES thereof, (C) of the original epitope hC5a position 68-74 (SEQ ID No: 3) and a VARIOTOPE thereof, (D) of the original epitope hC5a position 55-74 (SEQ ID No: 4) and a VARIOTOPE thereof.

FIG. 2 shows the inhibitory activity of the immune sera of mice which were vaccinated with the VARIOTOPES SEQ ID Nos: 5-23 in relation to the original epitope sequences, which is depicted as 100% (SEQ ID Nos: 1-4). FIG. 2 (A) shows the inhibition of immune sera induced by the original epitope hC5a position 65-74 (SEQ ID No: 1) and VARIOTOPES thereof, (B) of the original epitope hC5a position 63-74 (SEQ ID No: 2) and VARIOTOPES thereof, (C) of the original epitope hC5a position 68-74 (SEQ ID No: 3) and a VARIOTOPE thereof, (D) of the original epitope hC5a position 55-74 (SEQ ID No: 4) and a VARIOTOPE thereof.

FIG. 3 shows the assessment of the inhibitory activity of the antibodies induced by VARIOTOPES of the 12 amino acid long C-terminal fragment of hC5a (SEQ ID No: 2) where R at position 74 of hC5a was exchanged by amino acid residues of different characteristics (SEQ ID Nos: 21, 24-38).

FIG. 4 shows the assessment of the inhibitory activity of the antibodies induced by VARIOTOPES of the 12 amino acid long C-terminal fragment of hC5a (SEQ ID No: 2) where H at position 67 of hC5a was exchanged by amino acid residues of different characteristics (SEQ ID Nos: 17, 39-55).

Figure 6:
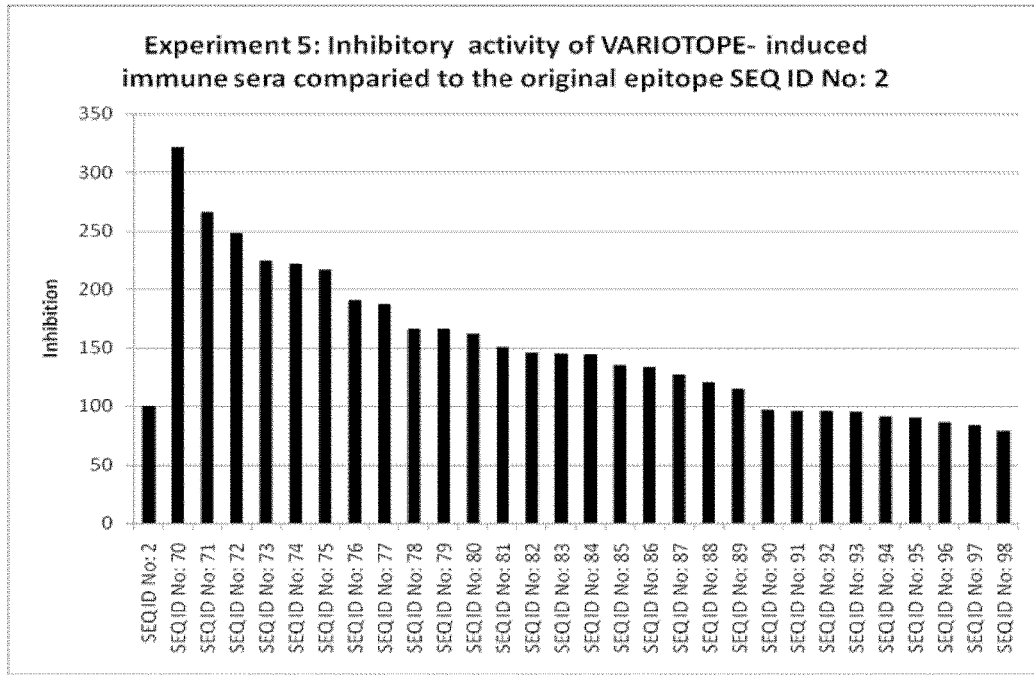

FIG. 6 shows the inhibitory activity of the antibodies induced by VARIOTOPES of the 12 amino acid long C-terminal fragment of hC5a (SEQ ID No: 2) where R at position 74 of hC5a and one or two additional amino acids at position 67 or 70 were exchanged by other amino acid residues (SEQ ID Nos: 70-98).

EXAMPLES

One object of the present invention is to develop a neutralizing active immune response against excessive human C5a in order to avert its pathological activity in chronic inflammatory disease or acute pathological situations.

In order to achieve this object so-called VARIOTOPES were designed and used for immunization in order to induce antibodies against the C-terminal neoepitope of the human C5a molecule. This neoepitope on C5a becomes accessible upon the cleavage of the C5 protein by the C5 convertase resulting in the small anaphylactic fragment C5a and C5b, a part of the membrane attack complex. VARIOTOPES are immunogenic peptides which are able to induce a humoral immune response to a protein of interest by resembling an epitope on the targeted protein. Hence, the advantage of VARIOTOPE vaccines is to elude the autotolerance to self antigens and to alleviate the risk of unmeant side effects which are prevalent by the use of self-antigens.

All peptides were chemically linked via a cysteine residue at the N-terminus to the protein carrier keyhole limped haemocyanin (KLH) and administered to mice together with Alum as an adjuvant. All immune sera which were obtained from mice either immunized with VARIOTOPES or the original C-terminal sequence of hC5a were analyzed for their ability to induce antibody titers and functional active antibodies against hC5a.

Material and Methods:

Immunization of Mice

BALB/c mice were used as a model system for hC5a-VARIOTOPE immunization experiments. Female BALB/c mice in the age of 6 to 8 weeks were primed and boost-immunized four times in biweekly intervals with KLH-conjugated VARIOTOPE vaccines (200 µl subcutaneously in phosphate buffer pH=7.4). Aluminum hydrogel was used as an adjuvant. Five to six mice were used for the immunization with the respective VARIOTOPE vaccine.

Immunogenicity Assay

The immune sera of the vaccinated mice were analyzed for their antibody response to the injected peptides (data not shown) and to the human C5a protein using the Enzyme Linked Immunosorbent Assay (ELISA). Antibody titers were determined as the sera dilution giving half-maximal binding (i.e. $OD_{max}/2$) and the mean titers of all mice per group are presented.

C5a Inhibition Assay

The inhibitory activity of the peptide or VARIOTOPE-induced antibodies against hC5a was assessed by the glucuronidase enzyme release assay using human U937 cells. U937 cells are differentiated with cyclic adenosine 3':5'-monophosphate and upon stimulation with human recombinant C5a protein β-glucuronidase is released. This effect can be blocked by the addition of hC5a specific antibodies or peptide-induced anti-hC5a immune sera. In more detail, U937 cells were differentiated for 5 days with 0.5 mM cyclic adenosine 3':5'-monophosphate (cAMP) in RPMI, 10% FCS. On day 5 the cells were pre-treated with cytochalasin B (2.5 µg/ml) for 10 minutes at 37° C. For each approach $1.8 \times 10^5$ pre-treated cells were stimulated either with 10 nM hC5a alone or with 10 nM hC5a plus 8% heat-inactivated serum (1 h at 56° C.) derived from mice immunized with different peptides or VARIOTOPES (SEQ ID Nos: 1-98 as indicated in Table 1 and 2) in a final volume of 120 µl HAG-CM buffer (20 mM HEPES pH=7.4, 125 mM NaCl, 5 mM KCl, 0.5 mM glucose, 1 mM $CaCl_2$, 1 mM $MgCl_2$, 0.25% BSA). After an incubation of 10 minutes at 37° C. the cells were pelleted, the supernatant was transferred to a 96-well microtiter plate, and diluted 1:1 with 0.01 M P-nitrophenyl-β-D-glucuronide (dissolved in 0.1 M sodium acetate pH=4.0) in a total volume of 150 µl. The microtiter plate was incubated for 1 h at 37° C. in the dark. Then the reaction was stopped by the addition of 0.4 M glycine buffer (pH=10.0). β-glucuronidase converts P-nitrophenyl-β-D-glucuronide to a yellowish color that is measured at 405 nm.

TABLE 1

Human C5a C-terminal epitopes used as a template for the generation of VARIOTOPES.

| Sequence identification number | Sequence |
| --- | --- |
| SEQ ID No: 1 | ISHKDMQLGR |
| SEQ ID No: 2 | ANISHKDMQLGR |
| SEQ ID No: 3 | KDMQLGR |
| SEQ ID No: 4 | VVASQLRANISHKDMQLGR |

TABLE 2

List of VARIOTOPES of hC5a C-terminal fragments (SEQ ID Nos: 1-4) where individual or multiple amino acids were replaced by different amino acid residues (underlined and indicated in bold).

| Sequence identification number | Sequence | Exchanged amino acids of hC5a |
| --- | --- | --- |
| SEQ ID No: 5 | ASHKDMQLGR | I65A |
| SEQ ID No: 6 | IAHKDMQLGR | S66A |
| SEQ ID No: 7 | ISAKDMQLGR | H67A |
| SEQ ID No: 8 | ISHADMQLGR | K68A |
| SEQ ID No: 9 | ISHKAMQLGR | D69A |
| SEQ ID No: 10 | ISHKDAQLGR | M70A |
| SEQ ID No: 11 | ISHKDMALGR | Q71A |
| SEQ ID No: 12 | ISHKDMQAGR | L72A |
| SEQ ID No: 13 | ISHKDMQLAR | G73A |

TABLE 2-continued

List of VARIOTOPES of hC5a C-terminal fragments (SEQ ID Nos: 1-4) where individual or multiple amino acids were replaced by different amino acid residues (underlined and indicated in bold).

| Sequence identification number | Sequence | Exchanged amino acids of hC5a |
|---|---|---|
| SEQ ID No: 14 | ISHKDMQLGA | R74A |
| SEQ ID No: 15 | AAISHKDMQLGR | N64A |
| SEQ ID No: 16 | ANASHKDMQLGR | I65A |
| SEQ ID No: 17 | ANISAKDMQLGR | H67A |
| SEQ ID No: 18 | ANISHKDAQLGR | M70A |
| SEQ ID No: 19 | ANISHKDMQAGR | L72A |
| SEQ ID No: 20 | ANISHKDMQLAR | G73A |
| SEQ ID No: 21 | ANISHKDMQLGA | R74A |
| SEQ ID No: 22 | KDMQLGA | R74A |
| SEQ ID No: 23 | VVASQLRANISHKDMQLGA | R74A |
| SEQ ID No: 24 | ANISHKDMQLGT | R74T |
| SEQ ID No: 25 | ANISHKDMQLGQ | R74Q |
| SEQ ID No: 26 | ANISHKDMQLGY | R74Y |
| SEQ ID No: 27 | ANISHKDMQLGM | R74M |
| SEQ ID No: 28 | ANISHKDMQLGG | R74G |
| SEQ ID No: 29 | ANISHKDMQLGV | R74V |
| SEQ ID No: 30 | ANISHKDMQLGK | R74K |
| SEQ ID No: 31 | ANISHKDMQLGS | R74S |
| SEQ ID No: 32 | ANISHKDMQLGH | R74H |
| SEQ ID No: 33 | ANISHKDMQLGN | R74N |
| SEQ ID No: 34 | ANISHKDMQLGL | R74L |
| SEQ ID No: 35 | ANISHKDMQLGW | R74W |
| SEQ ID No: 36 | ANISHKDMQLGF | R74F |
| SEQ ID No: 37 | ANISHKDMQLGP | R74P |
| SEQ ID No: 38 | ANISHKDMQLGD | R74D |
| SEQ ID No: 39 | ANISTKDMQLGR | H67T |
| SEQ ID No: 40 | ANISQKDMQLGR | H67Q |
| SEQ ID No: 41 | ANISEKDMQLGR | H67E |
| SEQ ID No: 42 | ANISSKDMQLGR | H67S |
| SEQ ID No: 43 | ANISKKDMQLGR | H67K |
| SEQ ID No: 44 | ANISNKDMQLGR | H67N |
| SEQ ID No: 45 | ANISIKDMQLGR | H67I |
| SEQ ID No: 46 | ANISRKDMQLGR | H67R |
| SEQ ID No: 47 | ANISMKDMQLGR | H67M |
| SEQ ID No: 48 | ANISVKDMQLGR | H67V |
| SEQ ID No: 49 | ANISYKDMQLGR | H67Y |

TABLE 2-continued

List of VARIOTOPES of hC5a C-terminal fragments (SEQ ID Nos: 1-4) where individual or multiple amino acids were replaced by different amino acid residues (underlined and indicated in bold).

| Sequence identification number | Sequence | Exchanged amino acids of hC5a |
|---|---|---|
| SEQ ID No: 50 | ANISLKDMQLGR | H67L |
| SEQ ID No: 51 | ANISWKDMQLGR | H67W |
| SEQ ID No: 52 | ANISGKDMQLGR | H67G |
| SEQ ID No: 53 | ANISPKDMQLGR | H67P |
| SEQ ID No: 54 | ANISFKDMQLGR | H67F |
| SEQ ID No: 55 | ANISDKDMQLGR | H67D |
| SEQ ID No: 56 | ANISHKDVQLGR | M70V |
| SEQ ID No: 57 | ANISHKDTQLGR | M70T |
| SEQ ID No: 58 | ANISHKDYQLGR | M70Y |
| SEQ ID No: 59 | ANISHKDLQLGR | M70L |
| SEQ ID No: 60 | ANISHKDKQLGR | M70K |
| SEQ ID No: 61 | ANISHKDHQLGR | M70H |
| SEQ ID No: 62 | ANISHKDRQLGR | M70R |
| SEQ ID No: 63 | ANISHKDWQLGR | M70W |
| SEQ ID No: 64 | ANISHKDSQLGR | M70S |
| SEQ ID No: 65 | ANISHKDFQLGR | M70F |
| SEQ ID No: 66 | ANISHKDNQLGR | M70N |
| SEQ ID No: 67 | ANISHKDPQLGR | M70P |
| SEQ ID No: 68 | ANISHKDGQLGR | M70G |
| SEQ ID No: 69 | ANISHKDDQLGR | M70D |
| SEQ ID No: 70 | ANISTKDMQLGA | H67T and R74A |
| SEQ ID No: 71 | ANISTKDMQLGQ | H67T and R74Q |
| SEQ ID No: 72 | ANISTKDMQLGS | H67T and R74S |
| SEQ ID No: 73 | ANISTKDMQLGM | H67T and R74M |
| SEQ ID No: 74 | ANISMKDMQLGN | H67M and R74N |
| SEQ ID No: 75 | ANISTKDKQLGM | H67T, M70K and R74M |
| SEQ ID No: 76 | ANISTKDMQLGH | H67T and R74H |
| SEQ ID No: 77 | ANISAKDMQLGA | H67A and R74A |
| SEQ ID No: 78 | ANISMKDMQLGA | H67M and R74A |
| SEQ ID No: 79 | ANISTKDKQLGA | H67T, M70K and R74A |
| SEQ ID No: 80 | ANISTKDAQLGA | H/T, M70A and R74A |
| SEQ ID No: 81 | ANISMKDMQLGS | H67M and R74S |
| SEQ ID No: 82 | ANISTKDVQLGA | H67T, M70V and R74A |
| SEQ ID No: 83 | ANISTKDMQLGN | H67T and R74N |
| SEQ ID No: 84 | ANISTKDMQLGK | H67T and R74K |
| SEQ ID No: 85 | ANISMKDMQLGM | H67M and R74M |

TABLE 2-continued

List of VARIOTOPES of hC5a C-terminal fragments (SEQ ID Nos: 1-4) where individual or multiple amino acids were replaced by different amino acid residues (underlined and indicated in bold).

| Sequence identification number | Sequence | Exchanged amino acids of hC5a |
|---|---|---|
| SEQ ID No: 86 | ANISTKDMQLGT | H67T and R74T |
| SEQ ID No: 87 | ANISHKDKQLGK | M70K and R74K |
| SEQ ID No: 88 | ANISMKDMQLGH | H67M and R74H |
| SEQ ID No: 89 | ANISAKDAQLGA | H67A, M70A, and R74A |
| SEQ ID No: 90 | ANISMKDKQLGK | H67M, M70K, and R74K |
| SEQ ID No: 91 | ANISHKDSQLGK | M70S and R74K |
| SEQ ID No: 92 | ANISMKDMQLGF | H67M and R74F |
| SEQ ID No: 93 | ANISIKDMQLGA | H67I and R74A |
| SEQ ID No: 94 | ANISMKDMQLGK | H67M and R74K |
| SEQ ID No: 95 | ANISLKDMQLGA | H67L and R74A |
| SEQ ID No: 96 | ANISHKDKQLGF | M70K and R74F |
| SEQ ID No: 97 | ANISMKDKQLGF | H67M, M70K, and R74F |
| SEQ ID No: 98 | ANISIKDMQLGK | H67I and R74K |

TABLE 3

Abbreviations for all amino acids and their side chain properties:

| Amino Acid | 3-Letter Code | 1-Letter Code | Side chain properties |
|---|---|---|---|
| Alanine | Ala | A | Nonpolar, aliphatic |
| Arginine | Arg | R | Positively charged |
| Asparagine | Asn | N | Polar, uncharged |
| Aspartic | Asp | D | Negatively charged |
| Cysteine | Cys | C | Polar, uncharged |
| Glutamic | Glu | E | Negatively charged |
| Glutamine | Gln | Q | Polar, uncharged |
| Glycine | Gly | G | Nonpolar, aliphatic |
| Histidine | His | H | Positively charged |
| Isoleucine | Ile | I | Nonpolar, aliphatic |
| Leucine | Leu | L | Nonpolar, aliphatic |
| Lysine | Lys | K | Positively charged |
| Methionine | Met | M | Nonpolar, aliphatic |
| Phenylalanine | Phe | F | Aromatic, nonpolar |
| Proline | Pro | P | Polar, uncharged, structural disruptor |
| Serine | Ser | S | Polar, uncharged |
| Threonine | Thr | T | Polar, uncharged |
| Tryptophan | Trp | W | Aromatic, nonpolar |
| Tyrosine | Tyr | Y | Aromatic, polar |
| Valine | Val | V | Nonpolar, aliphatic |

Example 1

Figures 1A, 1B:
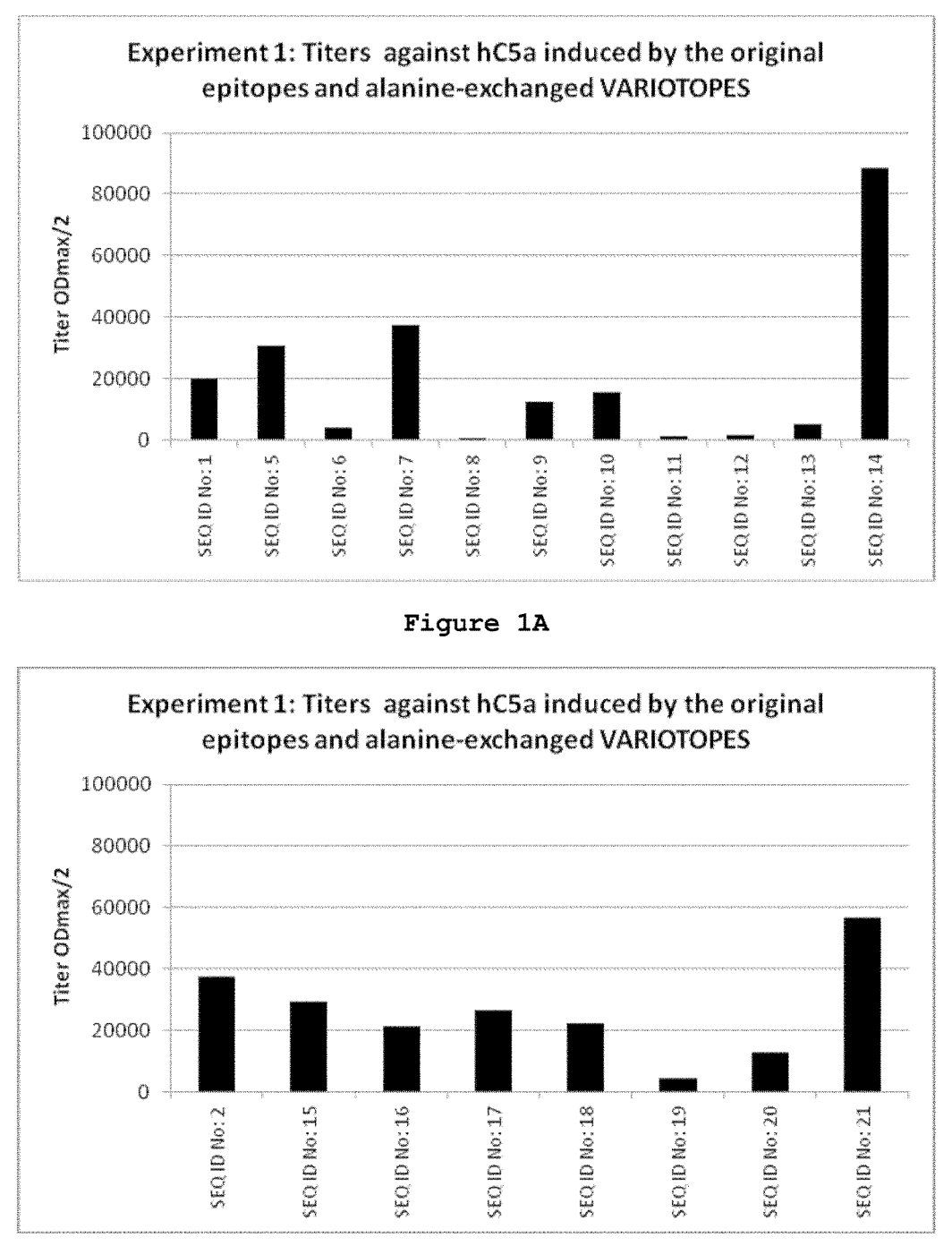

Alanine Scan of C-terminal Epitopes of hC5a SEQ ID Nos: 1-4 (Table 1) in Order to Define Positions Which can be Exchanged so that the Immunogenicity and the Ability to Induce Neutralizing Antibodies Against hC5a is Maintained or Even Increased Individual amino acids of the hC5a C-terminal epitope were substituted by an alanine residue and tested for their immunogenicity in comparison to the original epitope sequence. All VARIOTOPES clearly induced specific antibodies which bind to the injected peptide, however, the titers against the protein hC5a differ. The alanine exchange of hC5a position 66 (S66A), K at position 68 (K68A), Q at position 71 (Q71A), L at position 72 (L72A), and G at position 73 (G73A) clearly abrogated the induction of antibodies which recognize hC5a (FIGS. 1A and 1B; SEQ ID Nos: 6, 8, 11, 12, 13, 19, and 20). The original sequences SEQ ID Nos: 1-3 induce relatively high titers, whereas the titers induced by the VARIOTOPES SEQ ID Nos: 6, 8, 11, 12, 13, 19, and 20 drop to less than 13.000 ODmax/2, indicating that the amino acids S, K, Q, L, and G (hC5a position 66, 68, 71, 72, and 73) are crucial for the induction of hC5a specific antibodies (FIG. 1A and 1B, Table 1-2).

Figures 1C, 1D:
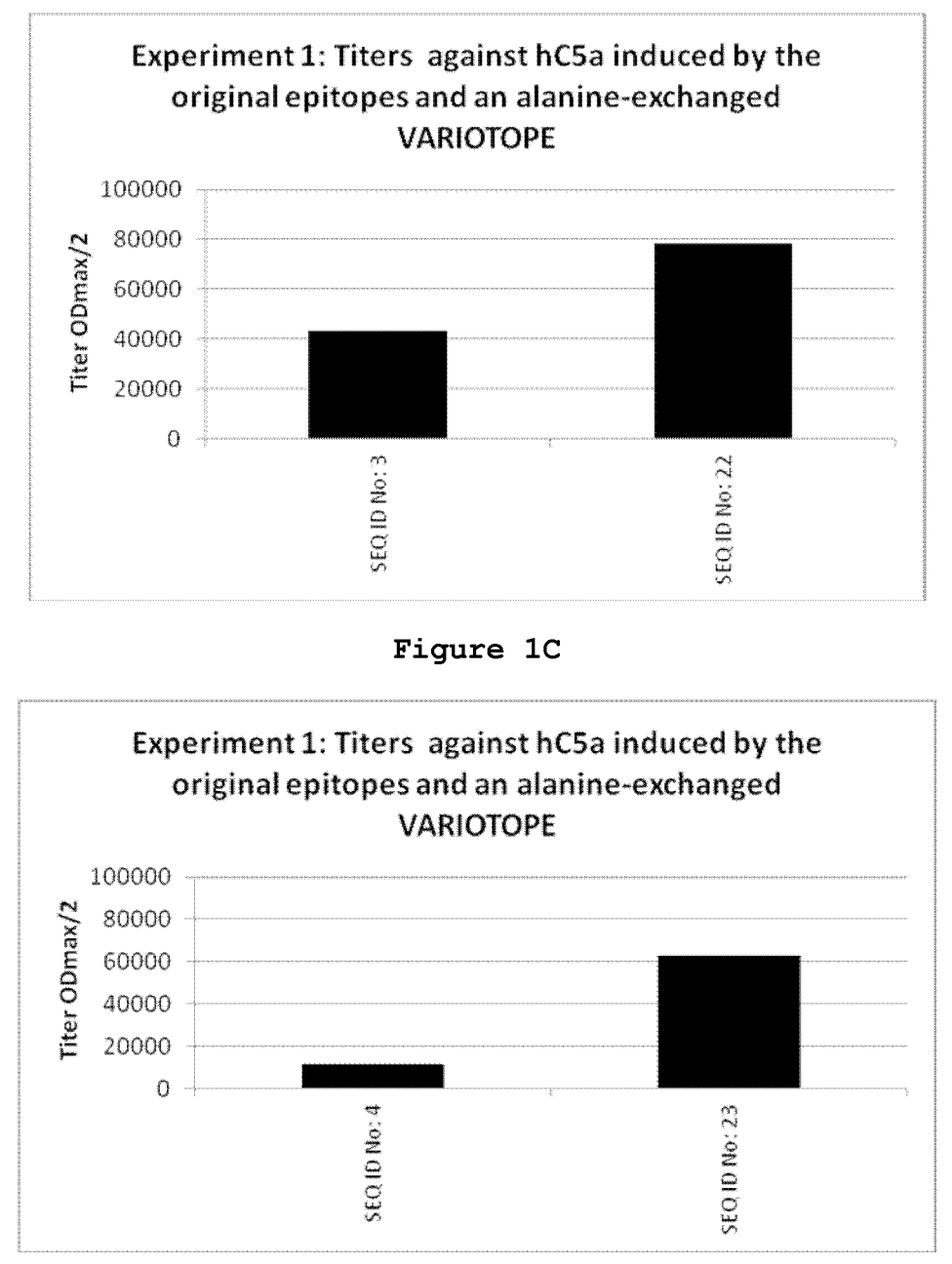

In contrast, the alanine substitution of R at the position 74 revealed a strong increase in anti-hC5a reacting antibodies. This was not only manifested for the 10 and 12 amino acid long C-terminal fragment of hC5a (FIG. 1A and 1B; SEQ ID Nos: 14, 21), but for all C-terminal hC5a VARIOTOPES of different length and the exchange R74A tested (FIG. 1C and 1D, SEQ ID Nos: 22-23). The titers of VARIOTOPES R74A ranged from 56.000 to 88.000 and reached up to a 5.5-fold increase when compared to the titer gained by the original sequence (FIG. 1D, SEQ ID Nos: 4 and 23). VARIOTOPES with the exchanges N64A, I65A, H67A, D69A, and M70A (SEQ ID Nos: 5, 7, 9, 10, 15-18) exhibit relevant titers against hC5a to a similar extent as the original epitopes SEQ ID Nos: 1-2 (FIGS. 1A and 1B, Table 1 and 2). In summary, the substitution of single amino acids within hC5a C-terminal epitopes of various length result in analog findings, indicating that the impact of particular amino acid residues on the immunogenicity against hC5a is only minor influenced by the length of the peptides. Especially the immunization with hC5a C-terminal fragments, where the R at position 74 was exchanged by A, resulted in significantly increased titers against hC5a when compared to the original epitopes. The peptide fragments which are used for vaccination comprise at least the last 7 C-terminal amino acids of hC5a in order to guarantee immunogenicity and may not exceed 19 amino acids, the defined length of the hC5a C-terminal neoepitope.

The inhibitory activity of the VARIOTOPES where individual amino acids were substituted by an alanine residue was assessed by the glucuronidase enzyme release assay. Briefly, β-glucuronidase is released from differentiated human U937 cells upon stimulation with hC5a and this effect can be blocked by the addition of anti-hC5a immune sera.

Figure 2A:
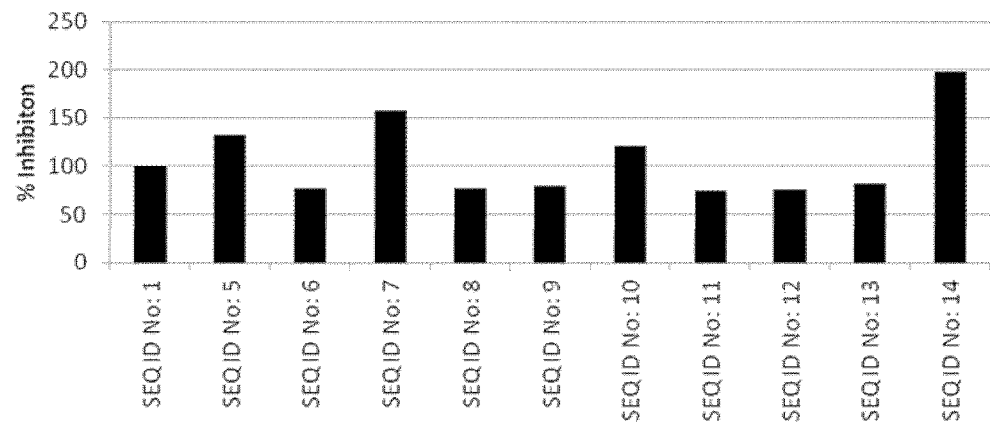
Figure 2B:
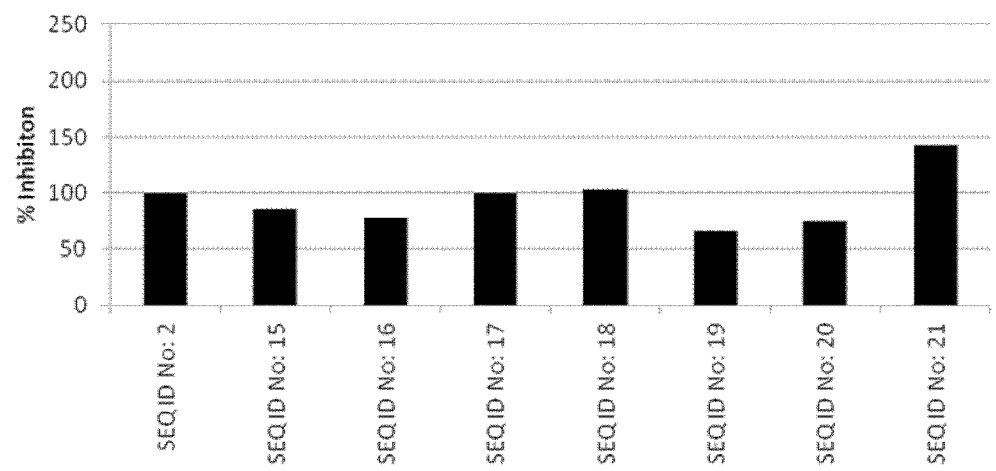
Figure 2C:
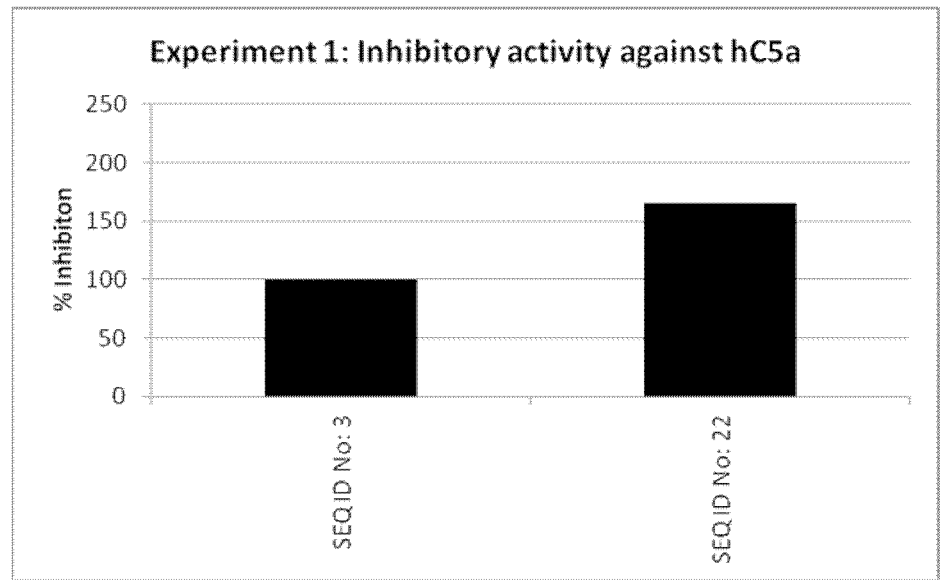
Figure 2D:
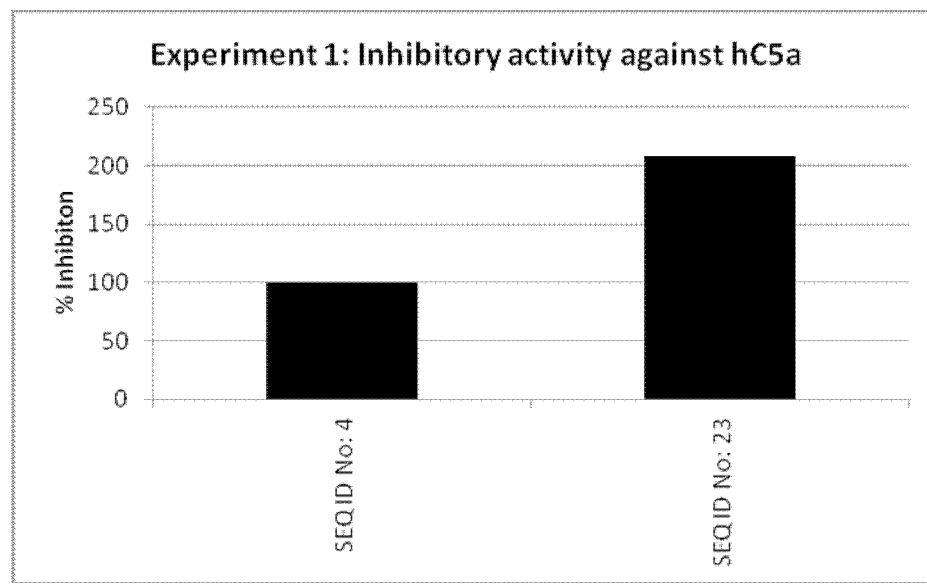

Immune sera induced by the VARIOTOPES R74A show the best inhibitory activity and compared to the original sequence (SEQ ID Nos: 1-4) up to a 2-fold increase in inhibitory activity was obtained (FIG. 2A-D, SEQ ID Nos: 14, 21, 22, and 23). Furthermore, the immune sera induced by SEQ ID Nos: 5, 7, 10, 17, and 18 revealed an inhibitory activity which either exceeds or is comparable to the signal obtained by the original epitopes (FIGS. 2A and 2B). Thus, the exchange H67A (SEQ ID Nos: 7, 17), M70A (SEQ ID Nos: 10, 18), and I65A, here only seen for the 10 (SEQ ID No: 5) and not for the 12 amino acid long (SEQ ID No: 16) hCa C-terminal VARIOTOPE, seems to be favorable for the induction of functional active antibodies against hC5a, however, the exchange R74A reign supreme albeit the different length of the VARIOTOPES (FIG. 2A-D).

The obtained protein titers against hC5a and the functional activity data based on the glucuronidase release assay show a good correlation. In the subsequent examples only the inhibitory activity of the immune sera (antibodies) induced by the original epitope and the VARIOTOPES thereof are shown, which in principal is more predictive for efficacy than the antibody titers alone.

Example 2

The key amino acid identified by the alanine scanning method was R at position 74 of hC5a which resulted in an up to two-fold increase in inhibition of hC5a (see FIG. 2). Thus, in a next experiment this position was systematically exchanged by a variety of amino acids having either similar or opposed features to the arginine residue (see Table 3). For this experiment the 12 amino acid long C-terminal epitope was selected as a template, because this fragment (FIG. 1B) induced higher titers against hC5a than the 10- or the 20 amino acid long fragment (FIGS. 1A and D) and show better inhibitory activity than the 7 amino acid long hC5a C-terminal fragment.

Figures 3, 4:
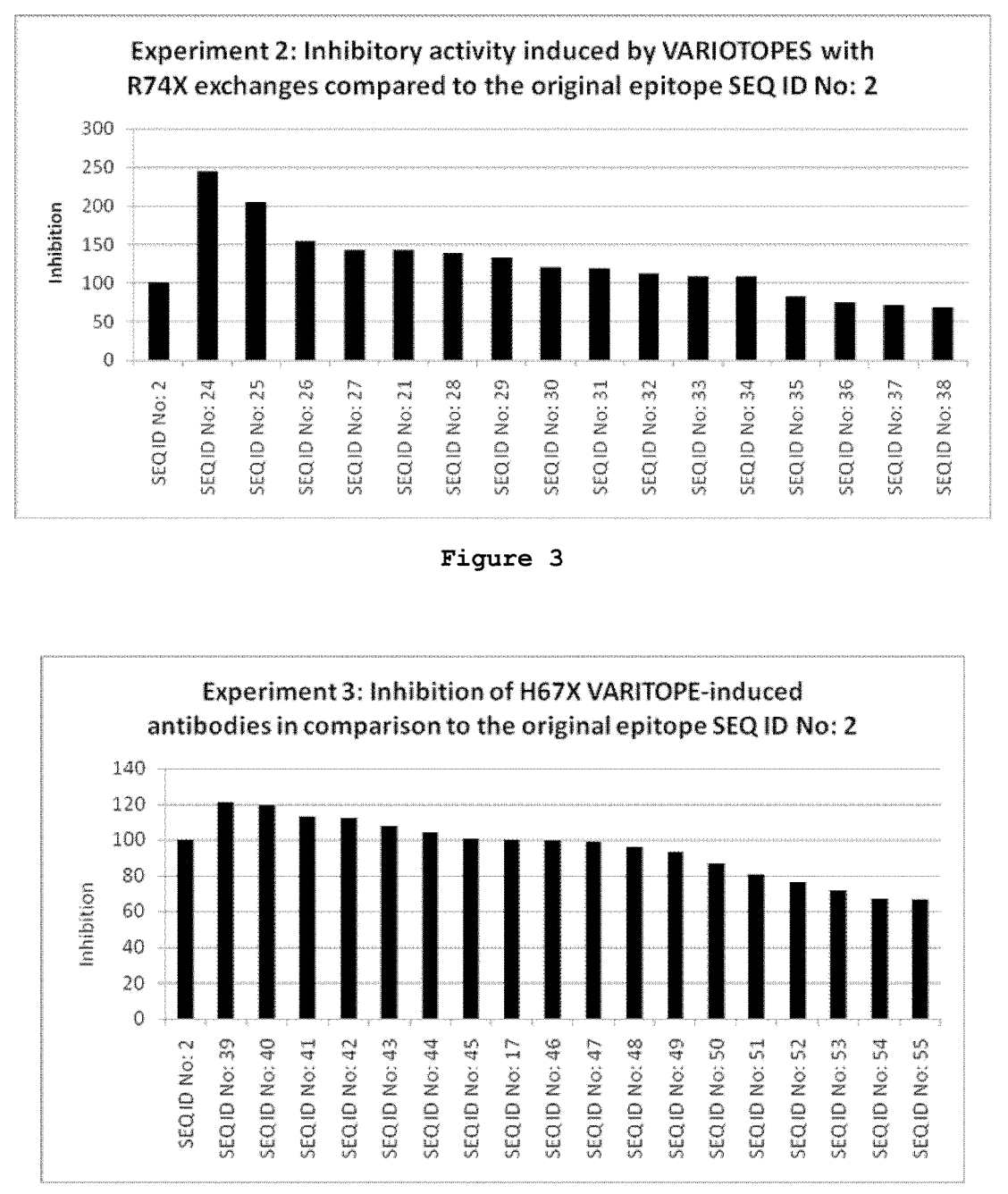

16 VARIOTOPES R74X of the 12 amino acid long C-terminal epitope of hC5a were tested for their immunogenicity and their ability to induce functional active antibodies. The immune sera obtained from VARIOTOPES with the exchanges R74T and R74Q showed the best inhibition in the glucuronidase release assay (FIG. 3, SEQ ID Nos: 24 and 25), followed by the exchange R74Y (FIG. 3, SEQ ID No: 26) and the replacements of R by the nonpolar, aliphatic amino acid residues M, A, G, and V (FIG. 3, SEQ ID Nos: 27, 21, 28, 29). VARIOTOPES where the R was replaced by a negatively charged amino acid (represented by R74D) or aromatic, nonpolar amino acids (W and F) and P, which is a structural disruptor amino acid, are not favorable to induce hC5a inhibiting antibodies (FIG. 4, SEQ ID Nos: 35-38).

Example 3

Histidine at position 67 of hC5a was another favorable exchangable position identified by the alanine scanning method. This position was again systematically exchanged by a variety of amino acids having either similar or opposed features to the histidine residue (see Table 3). 18 VARIOTOPES H67X of the 12 amino acid long C-terminal epitope of hC5a were tested for their immunogenicity and their ability to induce functional active antibodies (SEQ ID Nos: 17, 39-55).

The immune sera obtained from VARIOTOPES with the exchanges H67T and H67Q showed the best inhibition in the context of the glucuronidase release assay (FIG. 4, SEQ ID Nos: 39 and 40) with an increase of 20% when compared to the original sequence (SEQ ID No: 2) (FIG. 4). Immune sera induced by VARIOTOPES SEQ ID Nos: 41-47 exhibit slightly higher or comparable inhibiting activities as the original sequence SEQ ID Nos: 2. A clear negative effect on the inhibition of hC5a was seen for the immune sera induced by the VARIOTOPES SEQ ID Nos: 51-55 indicated in a reduction of 20 and more percent when compared to the original sequence (SEQ ID No: 2) (FIG. 4).

Example 4

Figure 5:
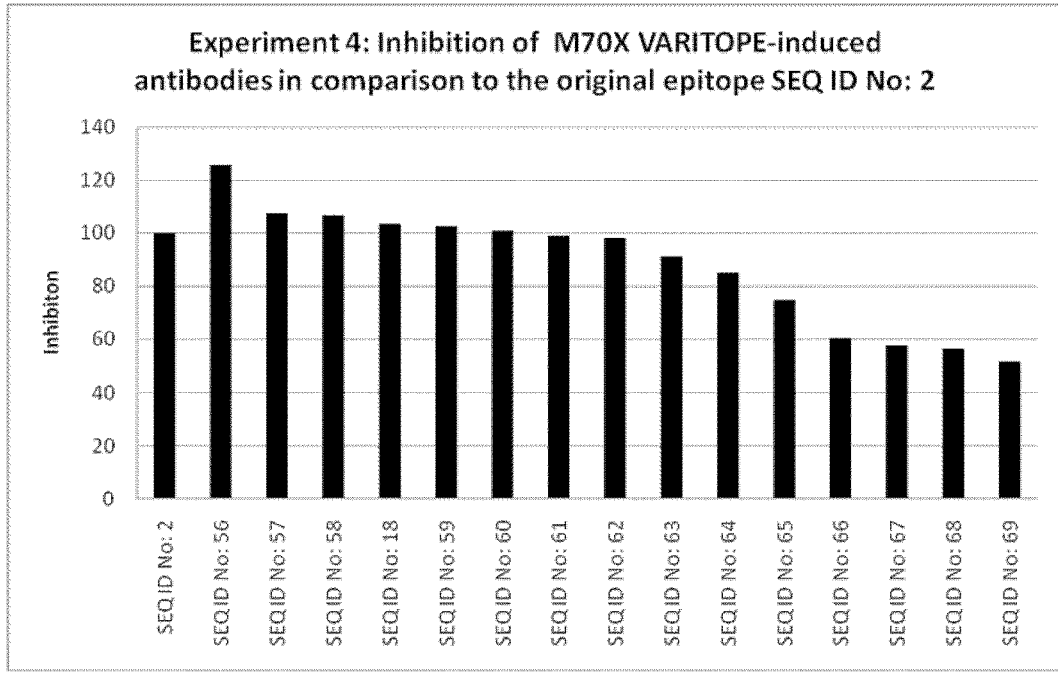
FIG. 5 shows the assessment of the inhibitory activity of the antibodies induced by VARIOTOPES of the 12 amino acid long C-terminal fragment of hC5a (SEQ ID No: 2) where H at position 67 of hC5a was exchanged by amino acid residues of different characteristics (SEQ ID Nos: 18, 56-69).

Methionine at position 70 of hC5a was the next amino acid which was systematically exchanged in order to define VARIOTOPES which are able to induce higher inhibitory activity against hC5a than the original 12 amino acid long C-terminal epitope of hC5a. 15 VARIOTOPES were tested and analyzed for their functional activity by the glucuronidase release assay. Immune sera induced by the VARIOTOPES SEQ ID Nos: 18 and 56-62 showed better or comparable inhibition signals than the immune serum induced by the original epitope SEQ ID No: 2 (FIG. 5). The VARITOPES SEQ ID No: 63-60 however, showed a stepwise decline in the inhibitory activity and are not favorable to induce functional active antibodies against hC5a.

Example 5

Amino acid exchanges at the position 74 of hC5a do have tremendous effects on the immunogenicity of C-terminal hC5a fragments and consequently also on the functional activity of the induced antibodies (see FIG. 3). This effect, however, was even more pronounced when the positions 67 or 70 or these both positions of the hC5a C-terminal epitope were exchanged in addition to favorable exchanges at position 74. In the following experiment VARIOTOPES containing the exchange R74X and an additional replacement at position 67 or 70, or both positions, respectively, were generated and tested for their immunogenicity. The exchange H67T, H67M, and H67A together with the replacement of R at position 74 by small nonpolar (A, M), polar uncharged (Q, S, N), and the positively charged H amino acid residues gained high titers and more than 1.5-fold reactive antibodies against hC5a when compared to the original epitope SEQ ID No: 2 (FIG. 6, SEQ ID Nos: 70-80). Advantageous exchanges at position 74 combined with favorable exchanges either at position 67, such as H67T, H67M, and H67A, or at position 70, such as M70K, M70A, and M7OV resulted in higher inhibitory activity when compared to the original sequence SEQ ID No: 2 (FIG. 6). Immune sera induced by the VARIOTOPES SEQ ID Nos: 90-98 were not favorable when compared to the original sequence, which is indicated by a reduced inhibitory activity (FIG. 6).

The invention claimed is:

1. A method for inhibiting C5a in a subject in need thereof, the method comprising administering to the subject a composition comprising a peptide,
   wherein the peptide consists of a sequence selected from the group consisting of ANISHKDMQLGA (SEQ ID No. 21), ANISHKDMQLGT (SEQ ID No. 24), ANISHKDMQLGQ (SEQ ID No. 25), ANISTKDMQLGA (SEQ ID No. 70), ANISTKDMQLGQ (SEQ ID No. 71), ANISTKDMQLGS (SEQ ID No. 72), ANISTKDMQLGM (SEQ ID No. 73), ANISMKDMQLGN (SEQ ID No. 74), ANISTKDKQLGM (SEQ ID No. 75), and ANISTKDMQLGH (SEQ ID No. 76),
   wherein the peptide is coupled or fused to a carrier comprising a T-cell epitope, the peptide optionally has at its N-terminus at least one cysteine residue bound directly or via a spacer sequence thereto and
   wherein the patient has a disorder involving the complement activation system.

2. The method according to claim 1, wherein the disorder is an inflammatory disease.

3. The method according to claim 2, wherein the inflammatory disease is selected from the group consisting of age-related macular degeneration (AMD), a neurodegenerative disorder, asthma, atherosclerosis, vasculitis, dermatitis, preferably psoriasis and urticaria, rheumatoid arthritis, Guillain-Barre syndrome, multiple sclerosis, antiphospholipid syndrome, hemolytic uremic syndrome, and systemic lupus erythematosus (SLE).

4. The method according to claim 2, wherein the inflammatory disease is a chronic inflammatory disease.

5. The method according to claim 1, wherein the disorder is selected from the group consisting of ischemia/reperfusion injury, acute lung injury, acute respiratory distress syndrome, sepsis, cancer, preeclampsia, recurrent spontaneous abortions, intra-uterine growth retardation and hemodialysis-associated thrombosis.

6. The method according to claim 1, wherein the disorder is Alzheimer's Disease.

7. The method according to claim 1, wherein the peptide has at its N-terminus, at least one cysteine residue bound directly or via a spacer sequence thereto.

8. The method according to claim 1, wherein the carrier is a protein carrier.

9. The method according to claim 8, wherein the protein carrier is selected from the group consisting of keyhole limpet haemocyanin (KLH), CRM197, tetanus toxoid (TT), protein D and diphtheria toxin (DT).

10. The method according to claim 1, wherein the composition further comprises an adjuvant.

11. The method according to claim 10, wherein the adjuvant is adsorbed to alum.

12. The method according to claim 1, wherein the peptide consists of ANISHKDMQLGA (SEQ ID No. 21).

13. The method according to claim 1, wherein the peptide consists of ANISHKDMQLGT (SEQ ID No. 24).

14. The method according to claim 1, wherein the peptide consists of ANISHKDMQLGQ (SEQ ID No. 25).

15. The method according to claim 1, wherein the peptide consists of ANISTKDMQLGA (SEQ ID No. 70).

16. The method according to claim 1 wherein the peptide consists of ANISTKDMQLGQ (SEQ ID No. 71).

17. The method according to claim 1, wherein the peptide consists of ANISTKDMQLGS (SEQ ID No. 72).

18. The method according to claim 1, wherein the peptide consists of ANISTKDMQLGM (SEQ ID No. 73).

19. The method according to claim 1, wherein the peptide consists of ANISMKDMQLGN (SEQ ID No. 74).

20. The method according to claim 1, wherein the peptide consists of ANISTKDKQLGM (SEQ ID No. 75).

21. The method according to claim 1, wherein the peptide consists of ANISTKDMQLGH (SEQ ID No. 76).

* * * * *